United States Patent
Palmer et al.

(10) Patent No.: US 6,368,862 B1
(45) Date of Patent: Apr. 9, 2002

(54) POLYMERASE I PROMOTER PLASMID AND VECTOR CONSTRUCTS

(75) Inventors: Theodore D. Palmer, Kirland; Brian M. McStay; A. Dusty Miller, both of Seattle; Ronald H. Reeder, Mercer Island, all of WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 07/845,937

(22) Filed: Mar. 4, 1992

Related U.S. Application Data

(63) Continuation-in-part of application No. 07/743,513, filed on Aug. 12, 1991, now abandoned.

(51) Int. Cl.$^7$ .............................................. C12N 15/63
(52) U.S. Cl. ...................... 435/455; 435/325; 435/353; 435/366; 536/23.1; 536/24.1
(58) Field of Search ............................. 435/69.1, 240.1, 435/240.2, 455, 325, 353, 366; 536/27, 23.1, 24.1

(56) References Cited

PUBLICATIONS

S. K. Jang et al (1989) J. Virology 63 (4): 1651–1660.*
Fleisher, S. and I. Grummt. 1983. Expression of an mRNA coding gene under the control of an RNA polymerase I promoter. *EMBO J*. 2: 2319–2322.
Grummt, I. and J.A. Skinner. 1985. Efficient transcription of a protein–coding gene from the RNA polymerase I promoter in transfected cells. *Proc. Natl. Acad. Sci. USA* 82: 722–726.
Smale, S.T. and R. Tijan. 1985. Transcription of Herpes Simplex virus tk sequences under the control of wild–type and mutant RNA polymerase I promoters. *Mol. Cell. Biol*. 5: 352–362.
Surmacz, E., O. Ronning, L. Kaczmarek and R. Baserga. 1986. Regulation of the expression of the SV40 T–antigen coding gene under the control of an rDNA promoter. *J. Cell. Phys*. 127: 357–365.
Surmacz, E., L. Kaczmarek, O. Ronning and R. Baserga. 1987. Activation of the ribosomal DNA promoter in cells exposed to insulinlike growth factor I. *Mol. Cell. Biol*. 7: 657–663.

Lopata, M.A., D.W. Cleveland and B. Sollner–Webb. 1986. RNA polymerase specificity of mRNA production and enhancer action. *Proc. Nat. Acad. Sci. USA* 83:6677–6681.

Rudenko, G., H.–M. M.Chung, V.P. Pham and L.H.T. Van der Ploeg. 1991. RNA polymerase I can mediate expression of CAT and neo protein–coding genes in Trypanasoma brucei. *EMBO J*. 10: 3387–3397.

Zomerdijk, J.C.B.M., R. Kieft and P. Borst. 1991a. Efficient production of functional mRNA mediated by RNA polymerase I in Trypanosoma brucei. *Nature* 353: 772–775.

Zomerdijk, J.C.B.M., R. Kieft, P.G. Shiels and P. Borst. 1991b. Alpha–amanitin–resistant transcription units in trypanosomes: a comparison of promoter sequences for a VSG gene expression site and for ribosomal RNA genes. *Nucl. Acids. Res*. 19: 5153–5158.

* cited by examiner

*Primary Examiner*—Remy Yucel
(74) *Attorney, Agent, or Firm*—Christensen, O'Connor, Johnson Kindness PLLC

(57) ABSTRACT rDNA promoter constructs useful in plasmids and vectors directing transcription of RNAs in a Pol I-specific manner constructed of four elements in a serial array: a first nucleotide sequence, capable of hybridizing under stringent conditions to an rDNA promoter element; a second nucleotide sequence, capable of hybridizing under stringent conditions to an internal ribosome entry signal (IRES); a third nucleotide sequence containing a coding region interest; a fourth nucleotide sequence containing a polyadenylation (polyA) signal sequence; a fifth rDNA enhancer element may be positioned upstream of the serial array. Also recombinant permissive cells and genetically engineered stable cell lines that contain the subject constructs.

5 Claims, 6 Drawing Sheets

SEQUENCE LISTING (1) GENERAL INFORMATION:

(iii) NUMBER OF SEQUENCES:5

(2) INFORMATION FOR SEQ ID NO:1:

(i) SEQUENCE CHARACTERISTICS:
      (A) LENGTH: 28

(B) TYPE:nucleotides (C) STRANDEDNESS: single (D) TOPOLOGY:linear (ii) MOLECULE TYPE:
      (A) DESCRIPTION:see application (as filed) page 32;
         oligonucleotide directed mutagenesis reagent (ix) SEQUENCE DESCRIPTION: SEQ ID NO:1:

AGGATCGTTT CCCATGGTTG AACAAGAT                                28

(2) INFORMATION FOR SEQ ID NO:2:

(i) SEQUENCE CHARACTERISTICS:
      (A) LENGTH: 10

(B) TYPE:nucleotides (C) STRANDEDNESS: single (D) TOPOLOGY:linear (ii) MOLECULE TYPE:
      (A) DESCRIPTION:see the application (as filed) page 33;
         EcoR1 linker (ix) SEQUENCE DESCRIPTION: SEQ ID NO:2:

CGGAATTCCG                                                   10

(2) INFORMATION FOR SEQ ID NO:3:

(i) SEQUENCE CHARACTERISTICS:
      (A) LENGTH: 30

(B) TYPE:nucleotides (C) STRANDEDNESS: single (D) TOPOLOGY:linear (ii) MOLECULE TYPE:
      (A) DESCRIPTION:see the application (as filed) page 33

(ix) SEQUENCE DESCRIPTION: SEQ ID NO:3:

GCATTTTGGG CCGCCGACAC GCTGTCCTCT                              30

(2) INFORMATION FOR SEQ ID NO:4:

(i) SEQUENCE CHARACTERISTICS:
      (A) LENGTH: 30

(B) TYPE:nucleotides (C) STRANDEDNESS: single

```
        (D) TOPOLOGY:linear (ii) MOLECULE TYPE:
         (A) DESCRIPTION:see the application (as filed) page 33

(ix) SEQUENCE DESCRIPTION: SEQ ID NO:4:

CCTATTGGAC CTGGGACACG CGGTCCTTTC                                              30

(2) INFORMATION FOR SEQ ID NO:5:
    (i) SEQUENCE CHARACTERISTICS:
        (A) LENGTH: 8

(B) TYPE:nucleotides (C) STRANDEDNESS: single (D) TOPOLOGY:linear (ii) MOLECULE TYPE:
         (A) DESCRIPTION:see the application (as filed) page 34;
             XbaI linkers (ix) SEQUENCE DESCRIPTION: SEQ ID NO:5:

CTCTAGAG                                                                       8
```

POLYMERASE I PROMOTER PLASMID AND VECTOR CONSTRUCTS

This application is a continuation-in-part application of pending patent application Ser. No. 07/743,513, filed Aug. 12, 1991 now abandoned.

This invention was made with government support under grants HL41212 and GM26624 awarded by the National Institutes of Health. The government has certain rights in this invention.

FIELD OF THE INVENTION

The invention relates generally to molecular biology and particularly to plasmid and vector constructs for obtaining RNA polymerase I-specific expression of a nucleotide sequence in a mammalian cell.

BACKGROUND OF THE INVENTION

Transcription in mammalian cells is initiated at promoter elements in the 5' region of a gene by polymerase binding at specific transcription initiation nucleotide sequences. The determination of which RNA polymerase, e.g., polymerase I, II, or III, will transcribe a given gene is also made at these specific promoter sequences. RNA polymerase II transcribes mRNA at many chromosomal loci, while several small structural RNAs are transcribed by RNA polymerase III. RNA polymerase I (Pol I) appears specific for ribosomal DNA (rDNA) promoter sequences that direct transcription of ribosomal RNA (rRNA).

mRNA transcribed from a chromosomal gene by RNA Polymerase II (Pol II) has the following significant structural features: namely, 1) a 5' trimethyl G "cap"; 2) an AUG codon in the proper sequence context to allow ribosomal initiation of translation; and, 3) a 3' poly A tail. The trimethyl G "cap" is thought to be necessary to allow ribosomes to recognize a transcript as mRNA. Ribosomes initiate translation at the "capped" 5' end of an mRNA, by scanning along the transcript until they encounter the first AUG codon in the proper sequence context. The 3' poly A tail of an mRNA is thought to contribute stability to an mRNA.

rRNA transcription differs from mRNA in noteworthy ways. rRNA is encoded from several hundred tandemly repeated copies of the ribosomal genes (rDNA) that are located in five different clusters at various chromosomal loci in mammalian cells. rDNA is also located in structural elements in the nucleus referred to as the nucleolar organizing center. Nucleoli form at this site when rDNA is actively being transcribed into rRNA, and a large cluster of nascent ribonucleoprotein particles forms around each active locus. These clusters are the structures visible in the light microscope that have been called "nucleoli." Processing of a ribosomal precursor rRNA (e.g., from a 28S precursor to 18S and 5.8S subunits) occurs in the nucleoli, and ribosomal proteins also associate with the rRNA before rRNA is transported from the nucleus to the cytoplasm as ribosomes. In addition, rRNA does not perform the functions of mRNA and is not translated by ribosomes into protein. Instead, rRNA is assembled into ribosomal proteins to form ribosomes which play a role in protein synthesis.

Features of Pol I transcription are notably different from the transcription of chromosomal genes by Pol II. For instance, an rRNA transcript synthesized by Pol I does not receive a trimethyl G "cap," instead, Pol I-specific transcripts retain a simple triphosphate at the 5' end and thus may not be recognized as mRNA by ribosomes. rRNA encoded by Pol I also has no AUG codons in a proper context, and rRNAs do not receive a 3' polyA tail. Current understanding of PolI transcription of rRNA initiated from an rDNA promoter has been reviewed recently (Reeder, R. H. 1991. In: *Transcriptional Regulation*, K. Yamamoto and S. L. McKnight, Eds, Cold Spring Harbor, N.Y., in press).

Promoters specific for RNA polymerase II are associated with chromosomal genes, and many such Pol II promoters have been isolated and used in expression plasmids and vectors. Several reports also describe experiments attempting to use a Pol I rDNA promoter to drive mRNA expression. Fleisher and Grummt (1; see the appended Citations) reported a mouse rDNA promoter attached to a gene for SV40 T-antigen, and Grummt and Skinner (2) reported a construct with a mouse rDNA promoter linked to a chloramphenicol acetyltransferase (CAT) marker gene. In the latter case, analysis of total cellular RNA reportedly showed high levels of transcript RNA, but only low levels of CAT activity were reportedly observed. A mouse rDNA promoter was also reportedly used by Surmacz et al. (4) to drive the SV40 T-antigen gene, but again the level of expression obtained was reportedly 5-to 10-fold poorer than that obtained with a Pol II promoter. Smale and Tijan (3) reportedly fused a human rDNA promoter to a gene for thymidine kinase (TK) marker gene, and although large amounts of transcripts were reportedly observed the RNA transcripts were reportedly unstable, not polyadenylated, and found largely in the nucleus rather than in the cytoplasm. Also, when the rDNA promoter was intentionally damaged in the latter study, i.e., by partial deletion of upstream sequences, it was revealed that transcription was initiated at two "cryptic" Pol II promoter sites in the plasmids. The finding of cryptic Pol II initiation sites raises the possibility that transcription attributed to rDNA promoters and Pol I may instead be mediated by Pol II transcription initiated at cryptic Pol II promoters. Lopata et al. (6) reported similarly that a mouse rDNA promoter driving a CAT gene expressed only low levels of CAT enzyme activity, and the only polysome-associated RNA reportedly came from aberrant initiation attributable to Pol II. The latter two reports appear to caution that extra care is needed to show that mRNA or protein expression is Pol I-specific, rather than mediated by another RNA polymerase initiating transcription at a cryptic promoter site(s). Thus, while rDNA promoter plasmids reportedly produced relatively large quantities of nuclear RNA transcripts, the transcripts remained in the nucleus and were inefficiently translated into protein product.

SUMMARY OF THE INVENTION

The invention provides rDNA promoter constructs useful in plasmids and vectors that direct transcription of RNAs in a Pol I-specific manner. The efficiency of protein production from the resulting transcripts approaches and in some cases surpasses that achieved with a strong Pol II-specific promoter. The nucleic acid constructs of the invention offer several advantages over previous Pol II vector systems, because rDNA promoters are highly active in essentially all cell types, and Pol I expression is under different cellular controls during growth and development than Pol II. The subject constructs provide quantitatively higher expression levels than achievable with previous Pol I constructs, and furthermore provide opportunities for constitutive expression.

The invention is embodied by constructs having four elements in a serial array: namely, a first nucleotide sequence, capable of hybridizing under stringent conditions to an rDNA promoter element; a second nucleotide sequence, capable of hybridizing under stringent conditions to an internal ribosome entry signal (IRES); a third nucleotide sequence containing a coding region of interest; and a fourth nucleotide sequence containing a polyadenylation (polyA) signal sequence. Pol I-specific expression of the second, third, and fourth nucleotide sequence is achieved by introducing the construct into a permissive cell. The latter process provides Pol I-specific expression levels that are higher than the levels achievable with an rDNA promoter construct lacking the IRES and polyA elements. The invention also provides genetically engineered stable cell lines that contain the subject constructs and that express the coding region third nucleotide sequence in a Pol I-specific manner. Pol I-specific expression can be verified by testing: a) that the expression is not substantially inhibitable by β-amanitin (i.e., an inhibitor of Pol II and Pol III); or, b) that the transcript polysome-associated RNA from the construct is 5'-trimethyl-Guanine-cap-deficient RNA; and/or c) that the expression is species-specific, e.g., a human rDNA promoter is expressed in human but not rodent cells, and a rodent rDNA promoter is expressed in rodent cells but not in human cells.

The subject constructs may be provided with a fifth element located upstream from the rDNA promoter element in the serial array. This fifth element is capable of hybridizing under stringent conditions to an rDNA enhancer element. Insertion of single or multiple copies of the fifth element at the upstream site enhances Pol I-specific transcription of the downstream (second, third and fourth) nucleotide sequences.

In an alternative embodiment, the subject construct has a linker region, containing one or more restriction sites or a polylinker region, in place of the coding region as the third nucleotide sequenc. The linker region faciliates insertion of a nucleotide sequence into the plasmid or vector.

DETAILED DESCRIPTION OF THE PREFERRED EMBODIMENT

Figure 1:
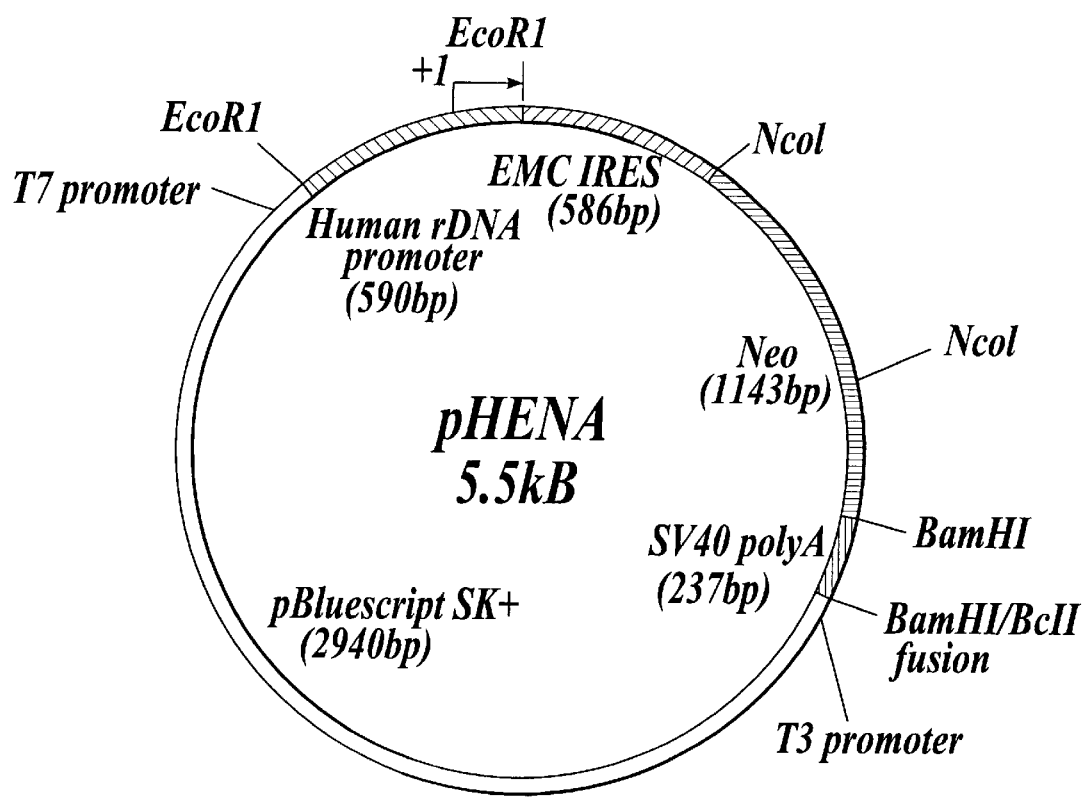
FIG. 1 shows the plasmid map with restriction site markers for a representative circularized plasmid construct (pHENA) containing in serial array: a human rDNA promoter element (H); an encephalomyocarditis virus IRES element (E); a coding region containing a reporter neomycin resistance gene (neo; N); and, an SV40 virus polyadenylation signal (polyA; A). The pHENA plasmid has been deposited on FEb. 21, 1992 with the American Type Culture Collection, Rockville, Md., and assigned the following accession number: namely, ATCC No. 75206.

The background art cited above concerns work in mammalian cells that seems to lead to at least two general conclusions. First, publications caution that spurious initiation by polymerase II can occur at cryptic Pol II promoter sites in a plasmid DNA, i.e., even though the DNA of the plasmid may contain an rDNA promoter (3,6). Therefore, to establish Pol-I specific expression of a coding region it would appear that special care must be taken to distinguish between protein production due to such spurious promoter initiation events and production due to bona fide initiation at an rDNA promoter site by Pol I. The second general conclusion is that some protein production driven by an rDNA promoter may have been obtained in several laboratories, but at a low level of expression relative to the expression usually obtained with a Pol II promoter. Quantitative estimates indicate that overall production from an rDNA promoter was at least 5- to 10-fold less than that obtained with a polymerase II promoter (4,7). In considering the problems of the prior art in obtaining Pol I-specific expression, at least the following four possibilities came readily to mind: namely, 1) Pol I transcripts may not be properly exported from the nucleus; or,
2) uncapped RNA transcripts might not be stable (e.g., they might be either rapidly degraded, or packaged into ribonucleoprotein that is not translated); or,
3) Pol I-specific RNA transcripts might not be segregated into appropriate processing and utilization pathways (e.g., it is not clear whether splicing, polyadenylation, and capping with a tri-methyl-G-cap are events that are physically linked in a cell in a transcription complex, or, whether the RNAs segregate into appropriate processing and utilization pathways solely on the basis of properties inherent to the transcript RNA itself); or, 4) RNA may not survive if it is not polyadenylated (e.g., since it is rRNA-like and rRNA has no polyA signal, and since polyadenylation is thought to play a role in the efficient transport of RNAs across the nuclear membrane and in affording protection from nucleases).

Prior to the invention it was not known that Pol I could be used to drive efficient production of a recombinant polypeptide in a cell. The specificity of the prior art Pol I vectors were in question (because of cryptic Pol II sites), and it was not known how to construct a vector that would be Pol I-specific. It was also not clear how to construct a plasmid or vector encoding Pol I-specific transcripts that could reach the ribosomal compartment because: a) it was not clear whether Pol I transcripts would survive in the nucleoplasm long enough to be transported (i.e. degredation by nucleases and/or processing into ribonucleoproteins); or, b) if they survived, whether they could be transported across the nuclear membrane; or, c) whether they could survive the transport process; or, d) if transported, whether they would still form polysomes (i.e. lacking a 5' methyl-G-cap, and competing with mRNA for ribosomes). Thus, prior to the invention it was difficult to envisage how introducing an rDNA promoter recombinant construct into a cell could lead to a significant level of expression of a gene of interest.

The studies presented in the Examples, below, demonstrate that deficiencies in prior Pol I vectors can be corrected by including both an IRES element and a PolyA element in the constructs. The success of the constructs of the invention suggest that much of the failure of the prior art constructs was probably attributable to poor message stabilization, improper RNA transport, lack of ribosomal binding and failure of translation.

As used herein the following terms are intended to mean:

The term "nucleic acid" as used herein means natural and synthetic DNA, RNA, oligonucleotides, oligonucleosides, and derivatives thereof. For ease of discussion, such nucleic acids are at times collectively referred to herein as "constructs," "plasmids," or "vectors." Representative examples of the nucleic acids of the invention include plasmid vectors such as expression, cosmid, and cloning vectors (e.g., pBR322, λ, and the like), viral vectors (e.g., retroviral, adenoviral, vaccinia, CMV, HIV viral vectors, and the like), and synthetic oligonucleotide molecules such as chemically synthesized RNA or DNA.

The term "in serial array" is used herein to mean that the recited nucleotide sequence elements are linked so that reading in 5' to 3' direction (5' to 3' with regard to the polarity of an RNA transcript from the constructs), the first nucleotide sequence appears first, followed by the second, third, and fourth.

The term "coding region" is used herein to mean that the recited nucleotide sequence contains the information content for a gene of interest (e.g., as provided by a cDNA, a synthetic oligonucleotide, a genomic DNA, and the like), and that the information content is transcribable into an oligonucleotide that is translatable into a recombinant peptide or polypeptide (e.g., protein). Representative examples of coding regions encoding polypeptides include DNAs and RNAs encoding: hormones (e.g., insulin, neuropeptides, and endorphins), receptors (e.g., insulin receptor), growth factors (e.g., PDGF), growth factor receptors (e.g., PDGF receptor), cellular structural proteins (e.g., cytokeratins, actin, myosin, and the like), extracellular matrix proteins and their receptors (e.g., fibronectin, integrins, adhesins, and the like), as well as plasma proteins (e.g., immunoglobulin or coagulation proteins such as Factors VII, VIII, IX, and the like). Transcription of the coding region in a recombinant cell produces an oligonucleotide product (e.g., RNA); translation of the oligonucleotide product (e.g., RNA) in a recombinant permissive cell produces a recombinant polypeptide.

"Encoding for a gene of interest" is used herein to mean transcription and translation of the recited "coding region," i.e., first transcription as an oligonucleotide (e.g., RNA) with information content for a recombinant polypeptide; and next, translation as the recombinant polypeptide. "Encoding for a protein of interest" is used to mean that the recited nucleotide sequences are linked so that: 1) the first nucleotide sequence (i.e., an rDNA promoter element) is capable of binding initiation factors and Pol I and mediating transcription of an RNA transcript of the downstream elements, i.e., the IRES element and coding region element; 2) the RNA transcript is capable of mediating internal entry of ribosomes at the IRES nucleotide sequence in the RNA; 3) the RNA transcript contains an AUG start codon in a proper context so that initiation of translation can occur; and, 4) translation of the RNA results in a recombinant polypeptide encoded by at least a portion of the nucleotide sequence residing in the coding region.

The term "capable of hybridizing under stringent conditions" is used to mean annealing a first nucleic acid to a second nucleic acid under stringent conditions (defined below). For example, the first nucleic acid may be a test sample, and the second nucleic acid may be the sense or antisense strand of an rDNA promoter, IRES, gene of interest, or an rDNA enhancer element. Hybridization of the first and second nucleic acids is conducted under standard stringent conditions, e.g., high temperature and/or low salt content, which tend to disfavor hybridization of dissimilar nucleotide sequences. A suitable protocol (involving hybridization in 0.1×SSC, at 68° C. for 2 hours) is described in Maniatis, T., et al., Molecular Cloning: A Laboratory Manual, Cold Springs Harbor Laboratory, Cold Springs, N.Y., 1982, at pages 387–389.

The term "rDNA" is used herein interchangeably with "ribosomal DNA" to refer to nucleotide sequences, including both transcribed (i.e., to rRNA) and non-transcribed sequences (e.g., control sequences), that are transcribable into a ribosomal RNA in a permissive mammalian cell (i.e., rRNA processed into the 18S, 5.8S, and 28S rRNAs, and found in mammalian cytoplasmic ribosomes). For example, in most cells (including mammals), rDNA occurs in tandemly repeated copies consisting of gene regions trascribable into ribosomal RNAs interspersed with intergenic spacers that contain control elements, e.g., promoters, enhancers, terminators, and possibly other elements that control transcription of the rDNA. The term "rDNA" as used herein is used to encompass both transcribable nucleotide sequences, and intergenic regions, promoters, enhancers, terminators, and other control elements that may have attendant advantages of changing the properties of the encoding by an rDNA promoter.

The term "rDNA promoter" is used herein to mean a DNA sequence that is capable of directing RNA polymerase I to initiate transcription at a specific site in a construct. For example, typical mammalian rDNA promoters are about 150 base pairs (bp) to many thousands of base pairs in length, are located at the 5' ends of genes transcribable into ribosomal RNA, and the rDNA promoter may overlap the site of transcription initiation by a few bp. As used herein, the term "rDNA promoter" refers to both the promoter and other functional promoter control units, e.g., a protective terminator upstream of the promoter, plus other enhancer elements that may be located in the intergenic spacer. Thus, a complete and functional "rDNA promoter," as used herein, may optionally include the rDNA promoter plus many kilobases of intergenic spacer regions. Representative examples are provided below and also include: a) nucleotides between −650 and 78 (relative to the transcription initiation site) of human rDNA promoter plasmid prHu4b, but exclusive of cryptic Pol II sites at −15 and −20; and, b) nucleotides between −500 and +1500 (relative to the transcription initiation site) of human rDNA promoter plasmid prHu3 (17).

The term "Pol I-specific manner," also abbreviated herein "Pol I-specific," as used herein means that a recited coding region is transcribed by RNA Polymerase I and not by RNA polymerases II, III, or any other cellular polymerase. Representative distinguishing features of RNA polymerase I in mammalian cells are: a) resistance to the fungal inhibitor alpha amanitin (i.e., alpha-amanitin at a concentration of less than about 10 $\mu$g/ml inhibits Pol II, or at about 100 $\mu$g/ml to about 200 $\mu$g/ml inhibits Pol III); b) relatively high species-specificity of transcription when compared with Pol II or Pol III. In a representative example of relatively high species specificity (e.g., as described in Example 2), a human Pol I promoter is not active in rodent cells (i.e., mouse, rat, or Chinese hamster) and a rodent Pol I promoter (i.e., mouse) is not active in primate cells (i.e., human or monkey). In this representative example a Pol II or Pol III promoter will have relatively low species specificity when the levels of expression are compared to the levels obtained with the Pol I promoter. "Pol I-specific" expression of RNA or protein may also, for example, not be inhibitable by S-adenosylhomocystein, but may be specifically inhibitable by low concentration of Actinomycin-D (e.g., 0.1 $\mu$g/ml), or by an effective concentration of an antibody that is inhibitory for Pol I mediated transcription.

The term "RNA Polymerase I" is used interchangeably herein with the term "Pol I" to mean a nuclear RNA polymerase (i.e., an assemblage of about 10 polypeptides) that specifically recognizes an rDNA promoter and is responsible in the cell for transcription of the 45S precursor to ribosomal RNA. In a representative example, Pol I (the enzyme, encoded by Pol I) is functionally distinguished from Pol II and Pol III by its promoter specificity, its resistance to alpha amanitin (see above), its species specificity (above), and the unique size of its larger polypeptide subunits.

The term "cryptic Pol II promoter(s)" is used to mean a "Pol II promoter" nucleotide sequence capable of initiating RNA polymerase II (Pol II) transcription that results in an oligonucleotide transcript of the downstream nucleotide sequences. The subject Pol II transcripts contain a 5'-trimethyl-Guanine-"cap", and are inhibitable by a amanitin (as described below).

The term "internal ribosome entry signal (IRES)" as used herein means a DNA or RNA nucleotide sequence, wherein the DNA encodes the RNA and the RNA is capable of binding with the translation initiation complex in a mammalian cell such that the downstream coding sequence in the nucleic acid is translated. Representative examples of IRES nucleotide sequences include 5' nontranslated regions (5' NTR) in picornavirus ribonucleic acid (e.g., EMCV, polio, and the like.) IRES form a regulatory stem loop structure in RNA that is capable of binding a ribosome initiation complex in the absence of a 5'-tri-methyl-G-cap. Representative IRES-containing constructs are disclosed in the prior patent application Ser. No. 07/743,513.

The term "splice site" as used herein refers to nucleotide sequences present in DNA at boundaries between intron and exon segments that direct the splicing reaction, (i.e., cutting of RNA at an upstream splice donor site and the rejoining of the RNA at a downstream splice acceptor site). The process of cutting and re-joining results in the removal of stretches of intron nucleotides from an RNA that has been transcribed from a DNA containing such a splice site. Splice donors, have a consensus sequence that is different from splice acceptors. Nucleotide sequences resident within the intron RNA nucleotides are also reported to be important for promoting the splicing reaction and are encompassed by the term "splice site" as used herein.

The terms "PolyA" is used herein to mean nucleotide sequences capable of directing "polyadenylation" at the 3' end of an RNA, e.g., by chemical reactions involving addition of multiple adenosine residues. "PolyA element," "PolyA region," and "PolyA signal" are used interchangeably herein to refer to DNA nucleotide sequences capable of encoding an RNA nucleotide sequence that directs polyadenylation, i.e., addition of a PolyA tail to an RNA. A representative example of a Poly A element is provided by the SV40 polyA region.

The term "oligonucleotide" is used interchangeably with oligonucleotide product to mean a nucleotide of about 9 to many hundreds of nucleotides in length, e.g., an RNA, that is a transcript of the gene of interest.

The term "recombinant polypeptide" as used herein means an amino acid sequence that is produced by use of recombinant DNA technology. "Recombinant polypeptides" of the invention have an amino acid sequence encoded by an oligonucleotide that is about 50% to about 100% homologous, and preferably about 80% to about 100% homologous with the nucleotide sequence encoded in nature by the gene of interest over a contiguous span of about 9 or more nucleotides. The term "homologous amino acid sequence" is used to mean an amino acid sequence related to the amino acid sequence of the natural gene product by: a) chimeric proteins formed by recombinant methods; or, b) conservative nucleotide substitution in the gene sequence encoding the gene product (e.g., G for C, A for T, etc.); or, c) substitution of one amino acid for another of like properties, e.g., a neutral amino acid for another neutral amino acid, one basic amino acid for another, one acidic for another, or one hydrophobic amino acid for another, and the like; or d) chemical derivatization of the amino acid sequence, e.g., by methylation, sulfation, acylation, and phosphorylation of amino acids. Those skilled in the art will recognize the advantages to be gained by substitution or chemical derivatization of the recited recombinant polypeptide, e.g., improved shelf-life stability of the recombinant polypeptide, improved expression levels in recombinant cells, reduced toxicity for recombinant cells, and the like. The recombinant polypeptides of the invention can also be engineered for improved stability for use in in vitro translation systems and the like.

The term "permissive cell" is used to refer to a mammalian cell with the properties of: a) derivation from the same species, or a closely related species, to the cell from which the rDNA promoter is derived; b) capable of expressing the rDNA promoter nucleic acid constructs of the invention in a Pol I-specific manner; and, c) mammalian or non-mammalian cells (e.g., prokaryotic cells) derived from a nonpermissive species that have been genetically engineered to become permissive to Pol I-specific expression of a gene of interest (e.g., by introduction of a permissive factor(s) such as the species specificity factor(s) discussed in greater detail below). A representative example of a closely related species is provided by a human rDNA promoter that may be used in certain monkey cells, e.g., COS cells. Representative permissive cells into which the recited nucleic acid may be introduced, e.g., by transfection or transduction, include normal mammalian cells (e.g., fibroblasts, hepatocytes, bone marrow cells, neural cells, and the like) and malignant cells (e.g., carcinoma cells, sarcoma, leukemia, and the like.) Those skilled in the art will recognize that the permissive cells that are embodiments of the invention have uses as expression systems, e.g., for the protein encoded by a gene of interest, or as sources for preparing cell-free extracts for in vitro translation systems and the like.

The nucleic acids of the invention having the rDNA promoter, IRES, coding region, and polyA may be introduced into permissive cells by a variety of methods that are well known in the art, including transfection (e.g., with "naked" DNA, microinjection, $CaPO_4$, PEG, and the like) and transduction (e.g., with plasmid and viral vectors, and the like). Those skilled in the art will recognize that the nucleic acids of the invention may be advantageously constructed utilizing prokaryotic cells for eventual use in mammalian permissive cells.

The term "substantially inhibited" is used to mean that the transcription of the gene of interest in a permissive cell is inhibited less than about 1% to about 10% by a concentration of a Pol II inhibitor (e.g., α-amanitin or Pol II-specific antibody) that is not nonspecifically toxic to the permissive cell, but which inhibits Pol II-specific transcription in a test cell by about 80% to about 100%. Representative examples of assays that may be used to measure the level of inhibition in the permissive cell include but are not limited to: SDS-PAGE, Northern blotting, enzyme assay (e.g., using a β-galactosidase or alkaline phosphatase encoding nucleotide sequence as the gene of interest), or colony assay (e.g., using a selectable marker encoding drug resistance for the gene of interest).

The term "5'-trimethyl-Guanine-cap-deficient RNA" is used herein to mean an RNA that is lacking a "5' cap." The term "5' cap" is used interchangeably herein with "5' trimethyl G cap" to mean the structure at the 5' terminus of an RNA transcribed by a Pol II or Pol III that is characterized by having a guanine (G) nucleotide linked to the 5' terminus of the RNA strand in a 5'-5' condensation, i.e., forming the following structure: 3'-G-5' ppp5'-Terminal Nucleotide-3'-RNA polynucleotide strand.

The term "ribosomal DNA enhancer region" is used herein interchangeably with "rDNA enhancer" and "rDNA enhancer region" to refer to a region of the rDNA intergenic spacer that when placed adjacent to an rDNA promoter element increases the probability that the element will be active in promoting initiation of transcription by Pol I. Representative examples of enhancer regions in mammals consist of multiple short repeated DNA sequences that bind one or more of the Pol I transcription factors needed to establish a stable initiation complex at the rDNA promoter. In general, the more repeated elements that are present, the stronger is the enhancer. As used herein, ribosomal DNA enhancer region is used to include one or more spacer promoters that in representative mammalian enhancer elements are located upstream of the short repeated enhancer segments. The spacer promoters may increase the activity of the enhancer elements and it is desirable to include them as an element in a ribosomal DNA enhancer region or constructs prepared therefrom. Representative rDNA enhancer regions may be less species specific than the rDNA promoters that they enhance, e.g., enhancers from mouse or human rDNA may enhance either a mouse or human rDNA promoter. Representative examples of well-studied enhancer regions are those of the frog, *Xenopus laevis*, and of the mouse such as those described in Pikaard et al. (20). An enhancer region contains a short repeated element referred to herein interchangeably as "enhancer region element" or simply "enhancer element." The enhancer element acts to give adjacent rDNA promoters a competitive advantage in attracting the proteins needed to establish a stable initiation complex. The multiple rDNA genes present in a mammalian cell have multiple enhancer elements located within the spacer regions between genes. An enhancer element may be isolated from a spacer region and identified operationally by virtue of its ability to increase Pol I-specific expression of the gene of interest when the enhancer nucleotide sequence is inserted upstream from the rDNA promoter in a test plasmid or vector. Those skilled in the art will recognize that the enhancer elements be of a compatible type such that when combined in a construct the Pol I-specific expression of the gene of interest is increased.

The term "upstream" as used herein refers to a position in a DNA that is located 5' to the position specified with regard to the direction of transcription (i.e., located 5' in the RNA); and the term "downstream" as used herein refers to a position in a DNA that is located 3' to the position specified (i.e., located 3' in the RNA).

The term "linker region" as used herein refers to a nucleotide sequence having one or more restriction endonuclease sites, or a universal polylinker region, capable of receiving a nucleotide sequence of a gene of interest. Representative examples of restriction nuclease sites that may be incorporated include nucleotide sequences cleaved by Eco RI, Bam HI, Sal I, and the like. Those skilled in the art will recognize that it may be desirable to incorporate a pair of restriction sites that allow the 3' to 5' orientation of a DNA to be determined.

In a representative embodiment the invention provides constructs consisting essentially of a DNA that has in serial array a 5' rDNA promoter, an IRES element, a coding region, and a 3' PolyA signal. The constructs also optionally be constructed with a splice site, consisting of a splice donor and splice acceptor, located between the coding region and the 3' PolyA signal. The constructs of the invention are transcribed specifically, and efficiently, by mammalian Pol I, and not by Pol II or Pol III. The RNA transcripts from the construct are transported from the nucleus of mammalian cells into the cytoplasm where they are translated efficiently by ribosomes. During nuclear transport the polyA tail and optional splice site may confer additive and greater than additive advantages in efficiency of transport and/or decreased degradation by nucleases. Constructs containing in serial array a Pol II-specific promoter, an IRES, a coding region, and a polyA tail are disclosed in copending U.S. patent application Ser. No. 07/743,513, filed Aug. 12, 1991.

In summary, prior art constructs that reportedly contained an rDNA promoter, a reporter gene, and in some cases an SV40 polyadenylation signal, when introduced into mammalian cells reportedly encoded low levels of protein. The prior constructs lacked the IRES element, and the RNAs transcribed from them by Pol I should also lack a 5' "cap". There is also some question in the prior art as to what level of expression was actually achieved from these Pol I promoters because of the presence of the cryptic Pol II promoter sites within the Pol I constructs. The prior art constructs included an AUG in proper context and some of them included sequences that could have resulted in polyA addition to the 3' end of the transcript. Therefore, based on the present experiments it seems highly likely that the poor translation observed in the prior art may, surprisingly, be mostly corrected just by circumventing the cellular requirement for a trimethyl cap by inserting a functional internal ribosomal entry site into the construct. The experimental results presented in Example 1, below, show that constructs with an IRES element expressed about 4-fold to about 26-fold greater levels of protein encoded by a coding region than control plasmids lacking an operative IRES element. The results presented also show that constructs containing only the rDNA promoter, IRES, and coding region expressed 10- to 30-fold less protein than constructs that also had a 3' polyA signal. Embodiments of the invention with both the IRES and polyA elements provide Pol I-specific trancription that is substantially independent of any possible cryptic Pol I initiation sites and RNA polymerase II. In the experimental results reported below, 99% of the protein encoded by the subject vector is expressed independently of Pol II. The results were achieved with a construct that had a Pol I promoter but no Pol II promoter or cryptic Pol II promoter elements operably linked to effect transcription of the second, third, and fourth nucleotide sequences. The experimental results provided below also show that the embodiments of the invention provide constructs with a coding region that expresses a nucleotide sequence as efficiently at the protein-level (i.e., translation product) as a strong Pol II-specific retroviral LTR promoter.

It is, of course, contemplated that the subject constructs may be introduced into a permissive cell in combination with other constructs (e.g., a construct(s) having a Pol II promoter). In one illustrative example, the coding region of the subject construct contains the same gene of interest that is contained in a second construct having a Pol II promoter. When both the subject construct and the latter second construct are introduced into a permissive cell the recombinant cells may have the advantage of high level transcription of the genes of interest allowing protein production by both the Pol I and the Pol II promoter systems. The dual-recombinant cells have the advantage that if expression mediated by the Pol II promoter decreases with time (e.g., due to regulatory feedback mechanisms) the expression mediated by the Pol I promoter should remain constant. Skilled artisans will also recognize that such dual recognition systems will allow interactive regulation of Pol I- and Pol II-mediated expression. For example, proteins that regulate Pol II expression may be encoded by the subject Pol I specific constructs, i.e., driven by the rDNA promoter, and this expression should not be subject to feedback inhibitory controls, i.e., by the expressed regulatory protein. Similarly, regulatory proteins that control Pol I expression may be encoded by a Pol II construct, and they should not be subject to feedback inhibitory control. Several uses come to mind. First, the the Pol I construct encoding Pol II regulatory factors could be used to make the Pol II expression respond to growth dependent, and species specific signals that would normally alter expression of the subject Pol I-specific constructs. Second, cells containing both the Pol I and Pol II dual-regulatory systems may prove to express a gene of interest in a constitutive manner that is very resistant to regulatory controls. It will be recognized that expression of the subject Pol I-promoter constructs in such a dual-recombinant cell can be determined by inhibiting Pol II expression, e.g., with α-amanitin.

Embodiments of the invention offer unique advantages over previous Pol II vector systems. For instance, polymerase I promoters are highly active in essentially all cell types and may provide quantitatively higher expression levels. Polymerase I expression is under different controls than polymerase II, especially during growth and development, that may confer advantages of growth-specific or development-specific expression to the constructs of the invention. The Pol I constructs of the invention may also drive constitutive expression of a gene of interest because cells require a constant renewal of rRNA to maintain viability.

In still other embodiments, the subject constructs increase the level of Pol I-specific protein produced in a recombinant permissive cell relative to the expression levels observed in a cell that is transduced or transfected with a nucleic acid lacking the IRES element and containing only the rDNA promoter and coding region. Comparison of the expression levels of the constructs of the invention with other constructs may be conveniently measured about 24 hrs. to about 3 weeks, preferably about 48 hrs. to about 10 days, after introduction of the subject construct into the cell. Representative assays for determining the expression level of the gene include: SDS-PAGE, Northern blots, enzyme assays (e.g., using a gene of interest, or a marker gene, that encodes an enzyme such as β-galactosidase or alkaline phosphatase), and colony assays (e.g., using a gene of interest, or marker gene, that encodes a drug resistance or sensitivity marker). In a representative example the expression level of the gene of interest measured about 48 hours after transfection is about 2-fold to about 30-fold, preferably about 4-fold to about 30-fold greater, and most preferably 12-fold to 30-fold greater than the expression level achieved in the cell when the coding region is linked to the rDNA promoter and a polyA element (i.e., in the absence of the IRES); and, the expression level of the gene of interest measured about 48 hours after transfection is about 4-fold to about 60-fold, preferably about 9-fold to about 60-fold greater, and most preferably 15-fold to 60-fold greater than the expression level achieved in the cell when the coding region is linked to the rDNA promoter and an IRES element (i.e., in the absence of the polyA element).

The expression levels of the Pol I-specific constructs of the embodiments of the invention may also be conveniently compared with the levels of exprression obtained by a Pol II-specific construct. As exemplified below, (Examples 1 and 3), the subject constructs of the invention are capable of encoding protein from the coding region at about 30% to about 300%, about 50% to about 300%, and preferably about 60% to about 300% of the levels of protein obtained using a Pol II-specific promoter linked to the subject coding region, IRES, and poly A elements, (i.e., in the same permissive cell type).

The nucleic acid constructs of the invention are transcribed in a Pol I-specific manner, and although the RNA transcripts are 5'-trimethyl-Guanine-cap-deficient they are translated in an efficient manner by ribosomes in a mammalian cell. By translated in an efficient manner is meant that a high percentage of the RNA transcripts that are transcribed from the subject construct are also translated in a cell. In this case the percentage transcribed and translated may be determined using either a static measurement, (e.g., at a single point in time the percentage of the transcript RNA that is polysome-associated), or as a kinetic measurement, (e.g., as the change in levels of polysome-associated transcript RNA between a first and second time point). One representative static assay that may be used for measuring the efficiency of translation in the permissive cell includes steps to: a) determine the total level of transcript RNA in the cell (i.e., total transcript RNA); b) determine the total level of transcript RNA that is associated with polysomes (i.e., polysome associated transcript RNA); and, c) calculating the efficiency of translation by calculating the percentage of the total transcript RNA that is polysome-associated. A first representative kinetic assay that may be used for determining translation efficiency includes the following steps: namely, a) determine the amount of polysome-associated RNA specific to the gene of interest (i.e., polysome associated RNA probed in a Northern blot for the gene of interest; the results expressed in arbitrary densitometric units recorded by scanning the blot); b) determine the rate of synthesis of the gene product of interest (e.g., mg protein/min), e.g., by measuring the rate of incorporation of radiolabeled amino acids into the gene product in a given time period (e.g., by precipitating the gene product with a specific antibody); and, c) calculate the efficiency of translation of the gene transcript RNA in the cell by dividing the result in step b) by the amount of polysome-associated transcript RNA resulting from the measurement in step a), i.e., mg/protein/min/unit of polysome RNA. A second representative kinetic assay involves measuring the amount of protein produced between a first and a second time point in a first recombinant cell containing the construct of the invention (i.e., the serial array of rDNA promoter, IRES, coding region, and polyA), and comparing that level with the level obtained in a second recombinant cell containing a Pol II-driven coding region (e.g., pLNX; Examples 1–3, below).

The invention also provides recombinant cells constructed by introducing the recited nucleic acid constructs into a permissive cell. The recombinant cells may be selected to obtain clonal and mixed cell populations that express the coding region nucleotide sequence in a constitutive manner. Selection of the recombinant cells for cell populations that have constitutive expression of the gene of interest may conveniently be accomplished, e.g., by cloning, FACS sorting, panning and the like, followed by testing the selected cell population for constitutive expression. "Constitutive expression" as used herein means continual expression of the gene of interest in a manner that is not sensitive to normal cellular feedback regulatory signals (e.g., end-product inhibition of biosynthesis of a cellular enzyme). Constitutively expressed proteins are not subject to large (i.e., at least 2-fold) increases or decreases in the levels of expression in the presence of growth factors, or other cellular activation signals such as Phorbol esters, retinoids, and the like.

Use of the recited nucleic acids and recombinant cells of the invention has attendant advantages of tissue specific expression and growth dependent expression that will be discussed in the following paragraphs. In principle, cells in the different tissues could regulate Pol I transcription by altering either the levels or activity of the initiation factors in the transcription complex, i.e., UBF and SL1. In fact, however, when comparing cells from different tissues the activities of the transcription initiation factors seem to be relatively constant, and instead, cells appear to regulate Pol I transcription by altering the 'levels' of the initiation factors in a tissue-specific manner. Such alterations may be used by cells during development to set the number of rDNA genes active in different types of tissues. When the subject nucleic acids are introduced into cells derived from different tissue types, they may be expressed at different 'levels' in the different cells. In this case the differential levels of expression in cells from different tissues is termed herein "tissue-specific expression."

In contrast, cells apparently do not use levels mechanisms for making rapid changes in expression response to environment or growth rate. Rapid changes in RNA polymerase I transcription rates appear to be effected by changing the activity of Factor C which controls the ability of the Pol I to initiate at a preformed UBF-SL1-promoter complex. Factor C has not as yet been definitively purified nor cloned. However, its activity has been shown to rise and fall in concert with changes in the rate of a marker RNA transcription encoded by a vector with an rDNA promoter. In rapidly dividing cultured cells rRNA production is high (i.e., Pol I transcription is high) and Factor C is active. When cells slow down and cease dividing (due to contact inhibition, serum starvation, etc.) transcription by Pol I nearly ceases and Factor C becomes inactive. When the subject nucleic acids are introduced into cells growing at different rates, the gene of interest is expressed at different levels (i.e., there is greater expression in a rapidly growing cell than in a stationary nongrowing cell). The latter differential expression levels of the subject nucleic acid in growing and nongrowing cells are referred to herein as "growth dependent expression" of a gene of interest in a mammalian cell.

The term "growth dependent expression" is used herein to also mean that the level of expression of the gene of interest in the cell may vary as the result of events such as the stage of the cell in the cell-cycle, the cellular environmental conditions (e.g., starvation conditions in serum-deficient culture medium), and/or cellular contact-dependent growth inhibition (e.g., contact-dependent cells in tissue culture at confluency). In general, the growth-dependent expression of the gene of interest may be manifest as a higher level of expression of the gene in a rapidly dividing (i.e., growing) population of cells than in a nondividing population; or, as decreased expression as the cells stop dividing. A representative process for achieving growth-dependent expression of a gene of interest is provided by placing the recombinant permissive cells (i.e., containing the nucleic acid of the invention) under conditions where growth dependent expression of rDNA genes will occur in a normal cell (e.g., in conditions of serum starvation, and the like).

Use of the subject nucleic acids and recombinant cells has still other attendant advantages of "dominance" and "species specificity." The subject nucleic acid preferably contains one or more rRNA enhancer elements, an rDNA promoter, an IRES, a coding region and a polyA signal. The enhancer elements are placed 5' to the rDNA promoter nucleotide sequence and the nucleotide sequences are linked such that they encode for expression of the coding region. An rDNA promoter that has multiple enhancer elements adjacent to it has a much higher probability of forming a stable transcription complex than a promoter with a few or no enhancers nearby. Situations exist in nature in which interspecific hybrids are formed, e.g., by mating between a species whose rDNA has many enhancer elements and a species whose rDNA has fewer enhancer elements. In the hybrid offspring of such a cross, it is often observed that the rDNA with many enhancers is transcriptionally dominant (i.e., the maternal or paternal rDNA exhibits "dominance"). In extreme cases the dominant rDNA completely outcompetes the rDNA of the other species and causes it to be silent, thus, resulting in apparent "species specificity" for the rDNA promoter. The subject nucleic acids constructed with multiple enhancer elements may exhibit the property of "dominance" or "species specificity" when they are introduced into certain genotypes of cells. The recombinant cells constructed in this manner can also be selected (e.g., by cloning or sorting) for the cells having species-specific or dominant expression of the coding region nucleotide sequence.

The relative number of recombinant cells constitutively expressing a coding region nucleotide sequence may be greater in a population of cells transfected or transduced with a nucleic acid containing at least one rDNA enhancer element than in a population of cells transfected or transduced with a nucleic acid having only the rDNA promoter, IRES, coding region, and polyA signal. The relative number of recombinant cells expressing detectable levels of the coding region sequence may also increase as the number of enhancer elements is increased up to a maximum level permitted by the cell. In the extreme example, the subject constructs may be constructed to be silent in one species of cells but transcriptionally active in another. Fusing one cell with another, e.g., in forming a hybridoma cell line, may result in different levels of expression of the gene of interest in the resultant hybridoma cells (i.e., reflecting dominance or species specificity). Also, mating between individuals of two different species, or between individuals with different genotypes within a species, may result in different levels of expression of the gene of interest in the progeny, i.e., expression that appears to reflect "maternal" or "paternal dominance." In a representative example, transgenic animals may be constructed using the recited nucleic acid constructs of the invention. When the transgenic animals are mated with animals of a second genotype the expression levels of the gene of interest may be increased or decreased in the progeny. Those skilled in the art will recognize that the animals exhibiting desirable traits of high or low level expression of the gene of interest can be identified, e.g., by measuring the levels of gene product in the blood and tissues of the progeny.

The subject constructs also provide assay systems for cloning of the factors that account for species specificity or dominance. For example, "species specificity factor(s)" (SSFs) that control the expression of mouse rDNA promoters in rodent cells, and human in human cells but not mouse, may be cloned using the assays provided herein. For example, an assay for cloning an SSF may be conducted so that two plasmids or vectors are co-transfected or transduced into a mouse cell: namely, a first construct that has a human rDNA promoter in serial array with a neomycin resistance gene; and, a second construct that has a test human cDNA plasmid (or even a random oligonucleotide test sequence). Cells that are neomycin resistant (e.g., in G418) may express the human SSF(s) that is required for expression of a human rDNA promoter in the recombinant cell. Those skilled in the art will recognize that the cloned SSF may be useful for controlling expression of the constructs of the invention, e.g., by switching a nonpermissive cell into a permissive cell and thus providing a two-stage process for selection.

For example, in stage #1 a construct having a human rDNA promoter is introduced into a nonpermissive cell such as a rodent cell. In this case the nucleotide sequence in the coding region of the construct is not expressed because of species specificity. Next, in stage #2 a construct containing a nucleotide sequence encoding the human SSF(s) (e.g., pLTR-SSF(s)-PolyA) is introduced into the cell. Expression of the SSFs in the cell switches the cell from nonpermissive to permissive, i.e., for expression of the nucleotide sequence in the coding region. Such an SSF-directed two-stage selection system finds particular utility where it may first be desirable to select for cells expressing a selectable marker; e.g., a plasmid construct with both a mouse and human rDNA promoter may be constructed where the mouse rDNA promoter drives expression of a drug resistance gene, and the human rDNA promoter drives expression of the coding region. Under the latter conditions when mouse cells are transfected with the plasmid the cells may be first selected for drug resistance under conditions where the coding region is not expressed. Those skilled in the art will recognize that this has an advantage because cells are stressed during the drug selection process and joint expression of the coding region and the drug resistance gene may additionally stress the cell so that cell viability suffers. After the drug resistant clones of cells have been satisfactorily selected, the second SSF-directed stage of expression can be employed to convert the non-permissive mouse cell into a permissive cell producing the protein product of the coding region nucleotide sequence. Those skilled in the art will also recognize that it may be desirable to use the two-stage SSF-directed expression system for introducing a gene of interest into a patient with a first vector having species- incompatible rDNA promoters, e.g., mouse rDNA promoter in human, and then at a later date "triggering" expression from the mouse rDNA promoter by introducing a second vector containing an SSF into the patient that is capable of converting the non-permissive cells of the patient into permissive cells.

In considering the species-specificity conferred by the Pol I-specific rDNA promoter in the constructs of the invention, there is definitive evidence of specificity to the action of Pol I. In yeast, Pol I transcribes only large precursor rDNA to rRNA. Evidence leading to the same conclusion is available for mammalian cells although it is not as definitive. In vertebrate cells (frogs and mammals) the basis for this specificity may reside in two transacting protein factors that are required for Pol I to recognize an rDNA promoter and to initiate transcription (i.e., transcription initiation factors). These two factors are UBF and SL1. (SL1 is one of several names that have been applied to this factor by various labs and we will use it herein for convenience.)

UBF is a DNA binding protein that is dimeric in its most active form. UBF has been cloned from several species and depending upon the species of origin it has a monomer molecular weight of 82 to 97 kd. SL1 has yet to be definitively purified or cloned; however, it may consist of more than one polypeptide and it is known to be highly species specific. It has been reported that in some cases addition of SL1 to an in vitro transcription extract can alter the species specificity of the extract; i.e., SL-1 from species "A" added to the extract from species "B" may confer upon the extract the ability to transcribe a vector "A" rDNA into "A" rRNA. SL1 and UBF together form a stable complex that recognizes and binds the rDNA promoter. Apparently the stable complex of SL1 with UBF is recognized by Pol I and it is this recognition which allows Pol I to initiate transcription in a Pol I-specific manner. A third transcription initiation factor involved with Pol I transcription has also been identified, which we will call Factor C for simplicity since it has several names attributed to it by different laboratories. Factor C is not a DNA binding protein but behaves more like a loosely associated subunit of Pol I. Factor C apparently can exist in two alternate states. In one state, it functions to allow Pol I to recognize the stable complex of UBF and SL1 and to initiate transcription; and, in the other state, Factor C is "inactive" and Pol I is unable to initiate transcription even though the UBF-SL1 complex is formed and is bound at the rDNA promoter site in the DNA (i.e., UBF-SL1-promoter).

Transcription of the subject constructs by Pol I is regulated at two different levels. The first level of regulation involves formation of a stable complex between UBF, SL1, and the rDNA promoter. In most cells some protein component needed for complex formation appears to be limiting, and only a fraction (one-half or less) of the approximately 200 ribosomal genes in a typical mammalian cell have stable complexes and are potentially capable of being transcribed. Because there is a limiting component, all of the ribosomal genes in a cell are in competition for stable complex formation, and only a fraction are successful in this competition. Ribosomes and protein synthesis are needed in essentially all cells and therefore some level of RNA polymerase I transcription occurs in nearly all cells. The maximum number of potentially active rDNA promoters is set by the ability to form stable complexes between UBF, SL1, and the rDNA promoters. This appears to be a long-term control. Short-term responses to growth rate are mediated by changes by Factor C which controls the ability of RNA polymerase I to recognize the stable UBF-SL1 complex. RNA polymerase I itself appears to be in excess in most cells.

The embodiments of the invention providing constructs in which "sense" RNA is transcribed have been discussed above. The invention also provides constructs capable of encoding an antisense oligonucleotide (e.g., greater than about 9 nucleotides to about several hundred nucleotides) or RNA (e.g., from about several hundred nucleotides to many kilobases of nucleotides) in a Pol I-specific manner. Antisense oligonucleotides or RNA are encoded from nucleotide sequences that are introduced, i.e., in a reverse 5' to 3' direction, into the "linker region" of the constructs of the invention (i.e., the 5' to 3' orientation is reversed relative to the direction of transcription of the normal gene). The subject nucleotide sequences are capable of forming antisense oligonucleotides and RNA when such constructs are transcribed in a Pol I-specific manner. The antisense oligonucleotides and RNA transcribed in this manner is useful for inhibiting expression of a 'target gene' either at the transcription or translation level. For example, transcription of the subject constructs may produce an antisense transcripts that are capable of inhibiting transcription by inhibiting initiation of transcription or by competing for limiting transcription factors; or, the antisense transcripts may inhibit transport of the target RNA; or, the antisense transcripts may inhibit translation of the RNA of the target gene.

The invention also provides constructs capable of encoding chimeric proteins, i.e., from chimeric nucleotide sequences introduced into the linker region. The term "chimeric" as used herein means a nucleotide sequence assembled from more that one gene, or assembled from a single gene, e.g., by shuffling exons, removing introns, and the like. The nucleotide sequence residing in the linker region region of such constructs are expressed in a Pol I-specific manner. Pol I-specific expression is driven by the upstream rDNA promoter element and preferably with the use of one or more rDNA enhancer elements (i.e., promoter spacer elements and the like, above).

The rDNA enhancer elements that are resident in the rDNA promoter elements may optionally confer an advantage in transcription initiated at the rDNA promoter, i.e., over other rDNA promoters in the cell. Also, by controlling Factor C activity (for example, by keeping the cells in a rapidly growing state where Factor C is active), those skilled in the art will recognize that the embodiments of the invention can be used to generate high-level expression of a gene interest in a permissive mammalian cell. Since Pol I transcription occurs at some level in almost all cells, an rDNA promoter-driven gene is constitutively expressed at reasonable levels in nearly all cells and may be immune from the extinction observed with certain Pol II driven genes. Those skilled in the art will recognize that such constitutive expression may be useful to produce sense and antisense oligonucleotides or proteins.

"Species specificity" and interspecies hybrids with altered expression provided by the subject constructs will next be discussed. Indirect evidence suggests that the limiting component for ribosomal gene expression in mammalian cells is SL1. The subject nucleic acid constructs when introduced into a permissive cell are in competition for the transcription initiation complexes, SL1 and UBF. The enhancer elements act to give adjacent rDNA promoters a competitive advantage in attracting the transcription initiation factor proteins needed to establish a stable initiation complex. Situations exist in nature in which interspecies hybrids are formed by mating a species whose rDNA has many enhancer elements with a species whose rDNA has fewer enhancer elements. In the hybrid offspring of such a cross, it is often observed that the rDNA with many enhancers is transcriptionally dominant (i.e., maternal or paternal dominance). In extreme cases the dominant rDNA completely outcompetes the rDNA of the other species and causes it to be completely silent and resulting in apparent "species specificity" for the rDNA promoters. Those skilled in the art will recognize the utility of these properties of the constructs of the invention for altering expression of a nucleotide sequence (e.g., in the linker region or coding region) by somatic hybridization of cells (e.g., by cell fusion and the like) as well as by mating of one or more transgenic animals constructed by inserting the constructs that are embodiments of the invention into the germ cell line of the animal.

The constructs that are embodiments of the invention also provide assays for identifying and cloning the factors responsible for Pol I-specific "growth dependent expression" of a nucleotide sequence, e.g., for cloning factors such as Factor C. As discussed above, cells could regulate Pol I transcription by altering the 'levels' or 'activity' of the initiation factors in the transcription complex, i.e., UBF and SL1. In "growth dependent expression" (above) rapid changes in RNA polymerase I transcription rates appear to be effected by changing the activity of Factor C which controls the ability of the polymerase to initiate at a performed UBF-SL1-promoter complex. Factor C has not as yet been definitively purified nor cloned. However, its activity has been shown to rise and fall in concert with changes in the rate of recombinant vector RNA transcription from an rDNA promoter. For example, in rapidly dividing cultured cells ribosomal RNA production is high (i.e., Pol I transcription is high) and Factor C is active. When cells slow down and cease dividing (due to contact inhibition, serum starvation, etc.) transcription by polymerase I nearly ceases and Factor C becomes inactive.

The constructs that are embodiments of the invention are useful for molecular cloning and expression of Factor C, since the levels of expression from coding region(s) (or linker regions) placed downstream from an rDNA promoter may be related to the amount of Factor C expression in a cell. For example, those skilled in the art will recognize that Northern blots and Western blots may be compared to identify the proteins that increase as expression increases. The proteins that increase and decrease may next be tested for their ability to bind proteins of the UBF-SL1-promoter complex, and may also be tested for their ability to control the ability of the Pol I to initiate at performed UBF-SL1-promoter complexes. The cloned Factor C produced by the latter process may be useful for increasing expression levels of nucleotide sequences (i.e., coding region or linker region sequences) in the constructs that are embodiments of the invention. For example, multiple Factor C nucleic acid constructs (i.e., cDNA or genomic) may be introduced along with the constructs of the invention into permissive cells. In the latter case the Factor C construct is preferably linked to a promoter, e.g., a Pol I, Pol II or Pol III promoter. Expression of the constructs of the invention in the recombinant Factor C permissive cells may be "enhanced" relative to permissive cells that express a normal level expression of Factor C. In the latter case the term "enhanced" is intended to mean increased levels of expression, and/or improved growth-dependent expression, or developmental-stage specific expression of nucleotide sequences contained (i.e., the coding region sequences or sequences in the linker region) of the construct.

In the following studies constructs were evaluated for: a) Pol I-specificity of gene expression (i.e., to exclude any possibility of transcription initiated by Pol II); b) the levels of Pol I-specific expression relative to a strong Pol II promoter; and, c) the stability of the expression.

EXAMPLE 1 rDNA Promoter-Specific Expression of a Reporter Gene in Plasmid Constructs

Figure 2:
FIG. 2 shows the maps of constructs pHENA, pΔHENA, pHΔENA, pHEN, PMENA, pΔMENA, pMEN, pENA, pΔENA, and pEN that were prepared to establish that expression from the plasmid constructs was Pol I-specific, and not mediated by transcription at "cryptic" Pol II sites (as described in Examples I and II, and the *Materials and Methods*, below). The abbreviations used in the plasmid constructs are: H, human rDNA promoter element; M, mouse rDNA promoter element; E, IRES element; N, neo; A, polyA element; and Δ, which designates deletion of sequences in the after-named element, e.g., ΔH refers to deletions of nucleotide sequences in the human rDNA promoter element.
Figure 2:
Figure 2:
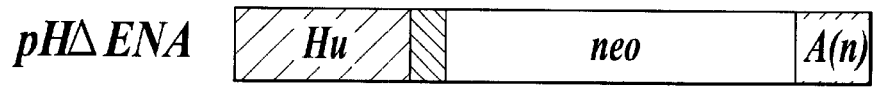
Figure 2:
Figure 2:
Figure 2:
Figure 2:
Figure 2:
Figure 2:
Figure 2:

To determine if RNA Polymerase I (Pol I)-specific rDNA promoter elements could be used to direct expression of proteins in cultured cells, a series of plasmid constructs were assembled containing a neomycin resistance reporter gene (Materials and Methods, below), and the constructs were introduced into rodent and human cell lines by calcium phosphate-mediated transfection. The plasmid constructs pHENA and pMENA (FIG. 1) contain a human or a mouse rDNA promoter region, respectively, driving expression of the bacterial neomycin phosphotransferase gene (neo). Because rDNA transcripts produced by Pol I do not incorporate 5' trimethyl-guanosine cap structures, an internal ribosome entry site (IRES) from the rat encephalomyocarditis virus (EMCV) was placed between the rDNA promoter regulatory elements and the neo gene to allow ribosome binding and translation of the neo reporter gene. A polyadenylation signal (polyA) from SV40 was also placed 3'of the neo coding sequences to provide message stabilization. To evaluate the role played by each of the genetic elements, and to determine which were necessary for high-level expression of neomycin phosphotransferase (NPT; Materials and Methods, below), inactivating deletions were introduced into each of the indicated elements of the construct, or alternatively the entire element was removed (plasmids contain Δ, indicating deletion) (FIGS. 1 and 2) and NPT expression was compared to the parent (non-deleted) rDNA promoter plasmids, namely, pHENA and pMENA. NPT expression was evaluated at the translational level (i.e., protein and enzymatic activity produced) rather than at the transcriptional level to avoid any possible errors related to non-translatable or non-transportable RNA (such as those encountered previously by others, above). The retroviral vector construct, pLNX, was used as a control for NPT production. This vector uses a strong polymerase II (Pol II) specific promoter from the Moloney murine sarcoma virus (MOMSV) long terminal repeat (LTR).

The expression of NPT from each different construct plasmid was evaluated by co-transfecting μg of the respective circular rDNA plasmid vector and 2 μg of the plasmid pRSV-βgal into rapidly growing cells. Transient expression of β-galactosidase and NPT was measured 48 hours after transfection. Since each transfection contained an equivalent amount of the neo reporter plasmid and the pRSV-βgal plasmid, it was possible to correct NPT activity for differences in the transfection efficiency of different cultures of cells by normalizing the NPT level to the level of β-galactosidase activity expressed by the cells.

Figure 3A:
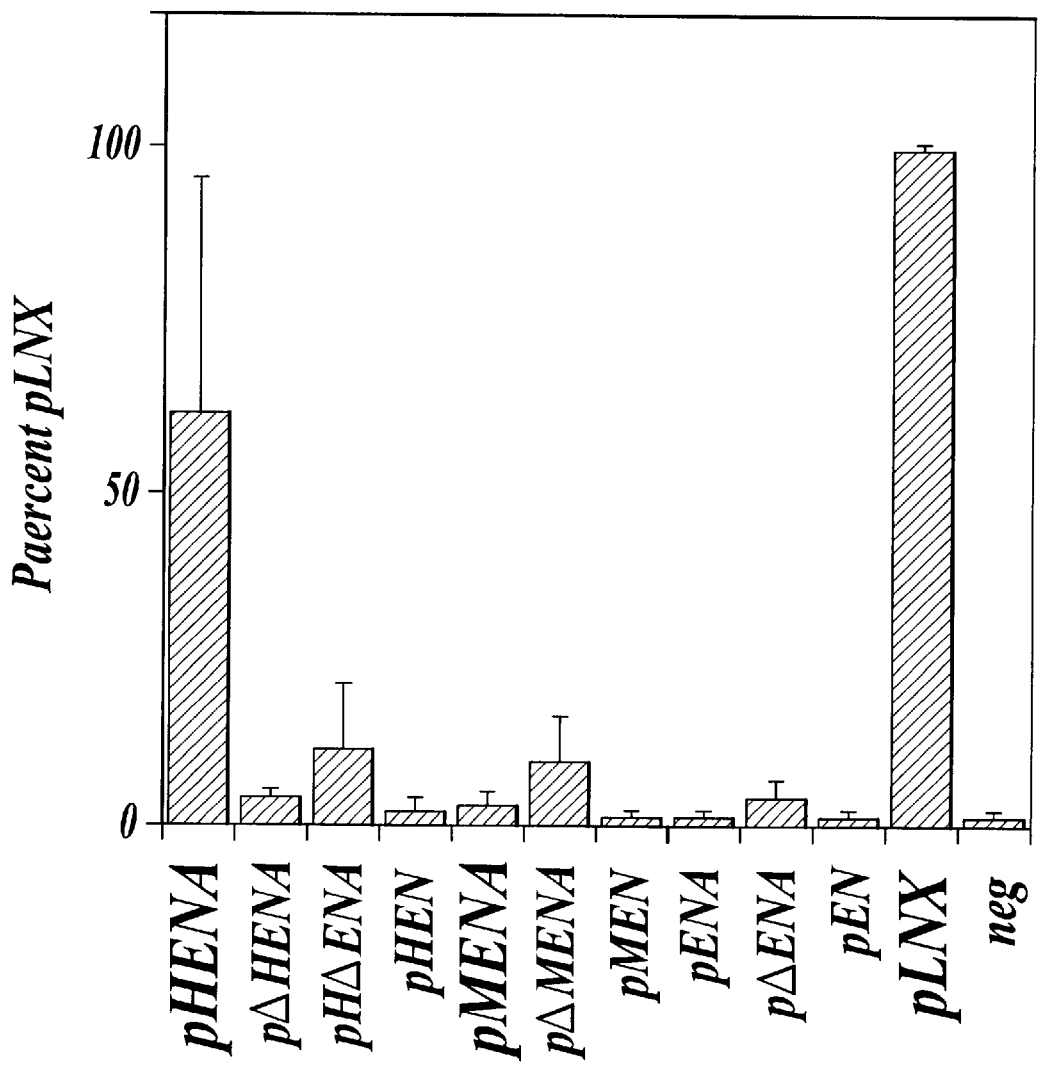
FIG. 3A shows the levels of Pol I-specific expression obtained in transient transfection assays from a reporter neo gene encoding the neomycin phosphotransferase enzyme (NPT) in human cells as measured by enzyme activity (as described in Examples 1 and 2). For comparative purposes the level of NPT activity is expressed as the percentage of the NPT activity obtained with a plasmid construct having a strong Pol II-specific promoter, i.e., pLNX (L, refers to a Pol II-specific retroviral LTR promoter).

The results presented in FIG. 3A and Table 1 show the levels of NPT activity recorded with each of the different rDNA promoter plasmid constructs. The data presented in FIG. 3A also allow a comparison to be made to the relative level of expression that can be obtained with the pLNX plasmid, i.e., containing the MuLV LTR that is a strong Pol II-specific promoter. The results show that in human cells NPT expression from the human rDNA promoter element (pHENA) is nearly equivalent to that obtained with a strong Pol II promoter (i.e., in pLNX). Removal of the human rDNA promoter element (i.e., pENA) abolished the NPT activity. Similarly, removal of either the IRES element or the polyA element (pHΔENA and pHEN, respectively) decreased expression. Deletion of sequences from −8 to +3 in the human rDNA promoter (pΔHENA) also abolished NPT activity. These results strongly suggest that the observed NPT expression was initiated at an authentic rDNA promoter site, rather than from a cryptic Pol II promoter in the construct, and that the expression observed was specific for the rDNA promoter element, i.e., rDNA promoter-specific.

TABLE 1

NPT Activity* in Transfected Cells

| Plasmid | Human | Rat |
| --- | --- | --- |
| pHENA | 15200 +/− 8700 | 990 +/− 700 |
| pDHENA | 1000 +/− 200 | 550 +/− 370 |
| pHDENA | 2700 +/− 2500 | 510 +/− 330 |
| pHEN | 500 +/− 500 | 40 +/− 40 |
| pMENA | 700 +/− 500 | 4660 +/− 2390 |
| pDMENA | 2200 +/− 1700 | 1360 +/− 700 |
| pMEN | 200 +/− 200 | 480 +/− 290 |
| pENA | 200 +/− 200 | 1170 +/− 670 |
| pDENA | 1000 +/− 700 | 290 +/− 70 |
| pEN | 200 +/− 200 | 110 +/− 40 |
| pLNX | 24900 +/− 12300 | 3670 +/− 2550 |
| Neg. Control | 500 +/− 200 | 150 +/− 40 |

*CPM/hr/mg protein, mean +/− S.D.

Figure 3B:
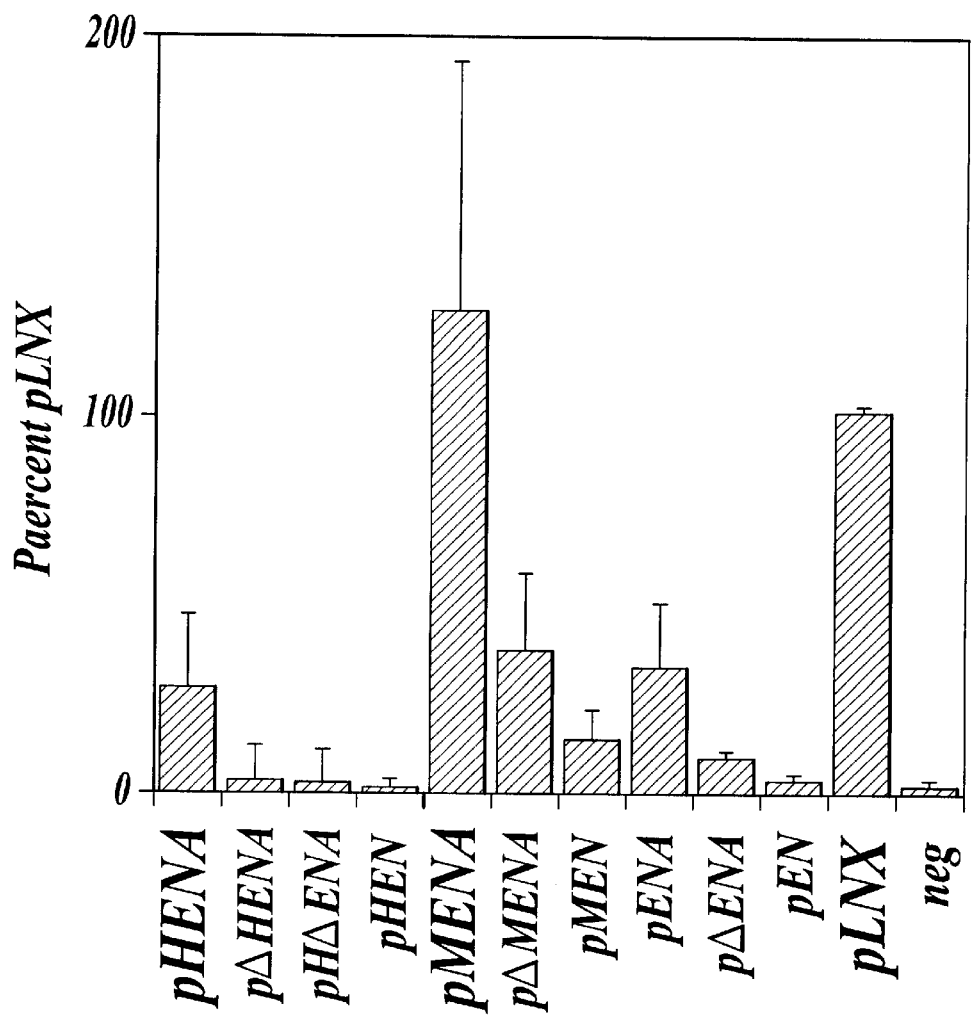
FIG. 3B shows the levels of Pol I-specific expression obtained in transient transfection assays from a reporter neo gene encoding the neomycin phosphotransferase enzyme (NPT) in rodent (i.e., rat) cells as measured by enzyme activity (as described in Examples 1 and 2). For comparative purposes the level of NPT activity is expressed as the percentage of the NPT activity obtained with a plasmid construct having a strong Pol II-specific promoter, i.e., pLNX.
Figure 4A:
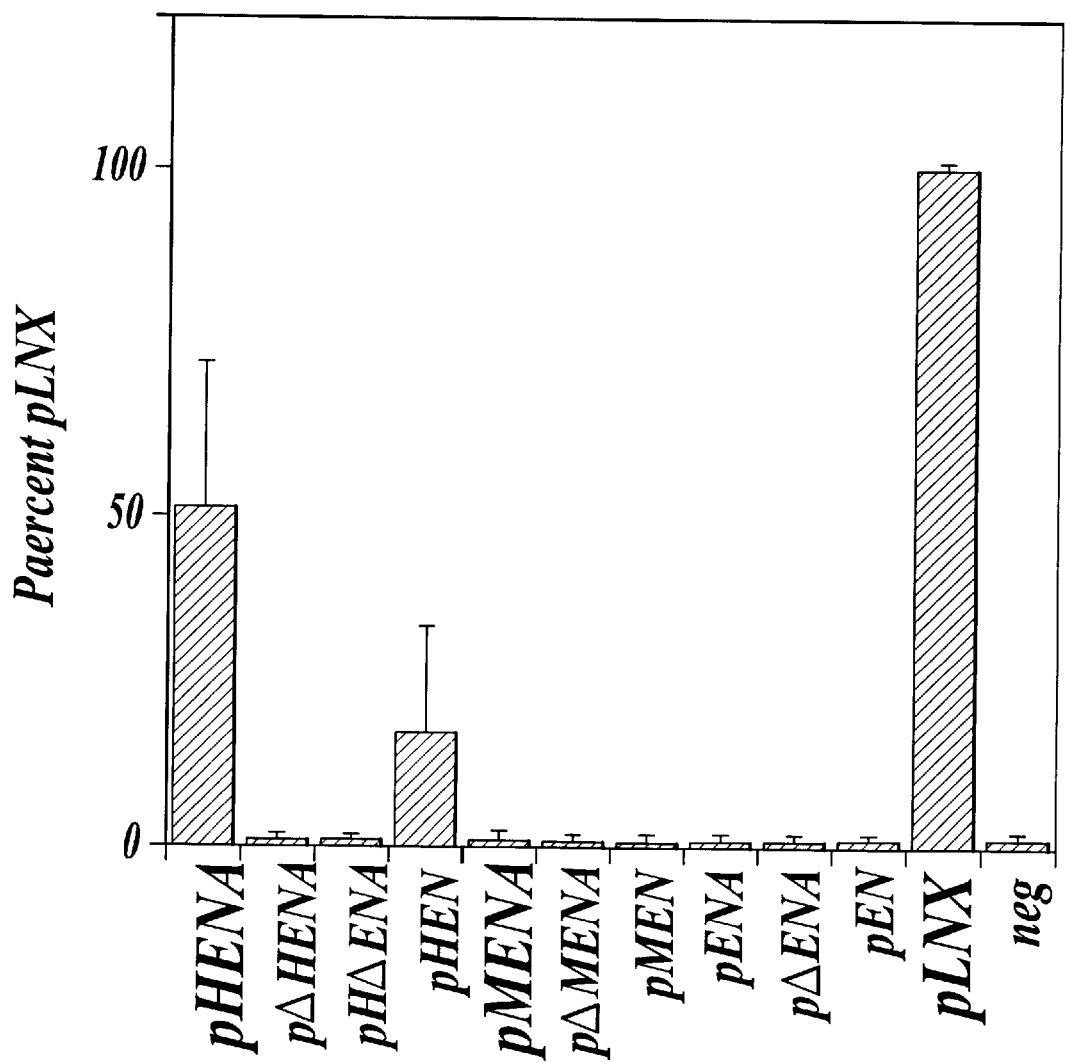
FIG. 4A shows the rate of formation of colonies of human cells with the constructs of the invention stably integrated into chromosomal DNA, and expressing in a Pol I-specific manner a reporter neo gene conferring resistance to the drug G418 (as described in Example 3). For comparative purposes the number of G418-resistant colonies of cells is expressed as a percentage of the number of colonies obtained with a plasmid construct having a strong Pol II-specific promoter, i.e., pLNX.
Figure 4B:
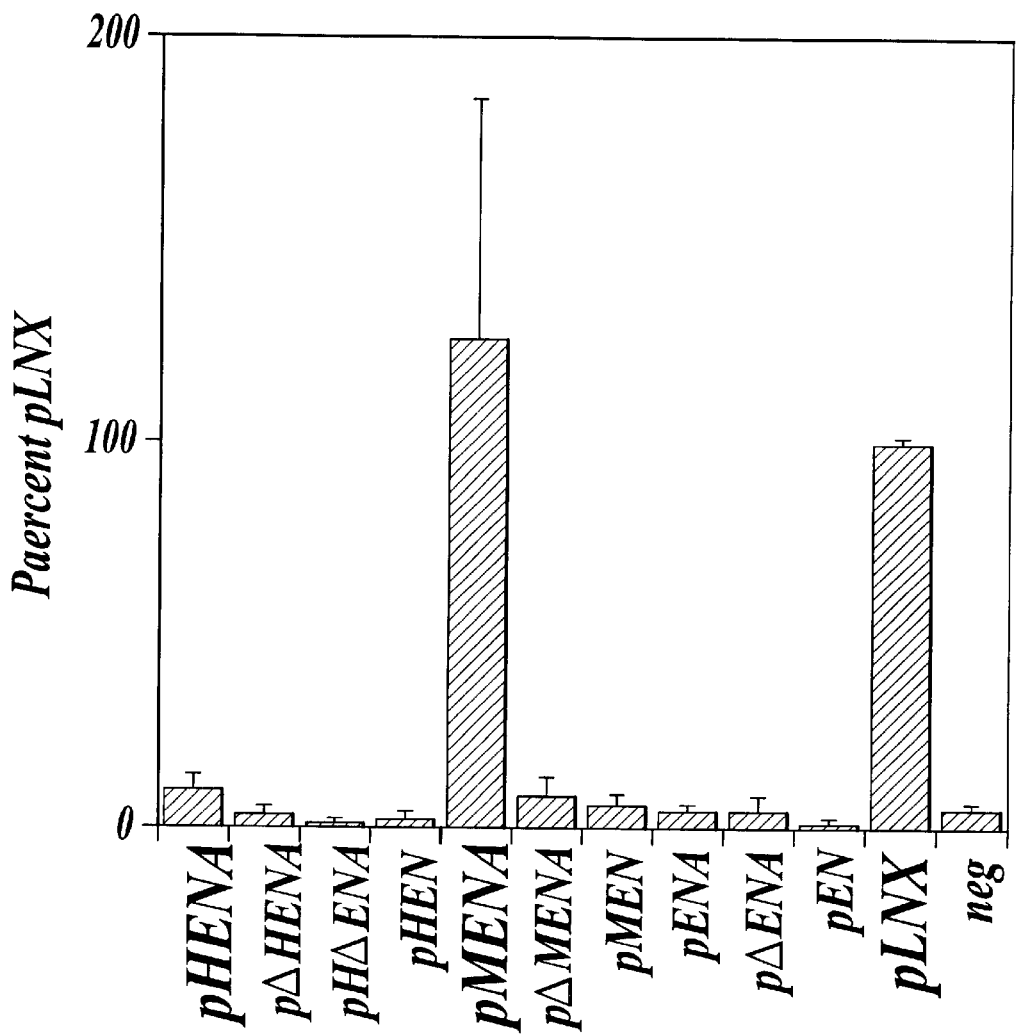
FIG. 4B shows the rate of formation of colonies of rat cells with the constructs of the invention stably integrated into chromosomal DNA and expressing in a Pol I-specific manner a reporter neo gene conferring resistance to the drug G418, as described in Example 3. For comparative purposes the number of G418 resistant colonies of cells is expressed as a percentage of the number of colonies obtained with a plasmid construct having a strong Pol II-specific promoter, i.e., pLNX.

In these studies the expression level of the neo gene determined in the enzyme assays 48 hours after transfection resulted in a level of expression of neo in the pHENA construct measured in different cultures that was about 30% to about 105% (range 30% to 105% in different cell cultures; mean +/−SD=61 +/−35%; FIG. 3A) of the levels achieved with the Pol II-specific pLNX construct. Similarly, the levels of neo expression for the pMENA construct in different cultures were about 55% to about 260% (range 55% to 260%; mean +/−SD=127 +/−65%; FIG. 3B).

The data also show (as summarized in Table 2) that constructs with an IRES element (i.e., pHENA or pMENA; FIG. 3A and FIG. 3B) expressed 4-fold to 26-fold greater levels of NPT than control plasmids lacking an operative IRES element (i.e., pHΔENA, FIG. 3A). In addition, plasmids constructed with a 3' polyA (i.e., pHENA or pMENA; FIG. 3A or 3B) expressed 10-fold to 30-fold greater NPT levels than plasmids lacking the polyA (i.e., pHEN and pMEN; FIG. 3A and FIG. 3B).

TABLE 2

Quantitative Role of IRES and PolyA Fold Decrease in NPT Activity

| Element Deleted | Human Cells | | Rat Cells | |
| --- | --- | --- | --- | --- |
| | Average | Range | Average | Range |
| IRES | 6 | 4–26 | n.d. | n.d. |
| PolyA | 31 | 15–52 | 10 | 9–11 |

EXAMPLE 2

Pol I-Specific Expression of a Protein Encoding Reporter Gene in the Coding Region of an rDNA Promoter Plasmid DNA Human and rodent rDNA promoters are known to be highly species-specific, i.e., being expressed only by human or rodent Pol I, respectively. The Pol I-specificity of the expression observed in Example 1 (above) was next examined. Species specificity of the expression was determined using human and mouse rDNA promoters that were tested in human and rodent cells. The results presented in FIG. 2b show that the NPT activity expressed from the rDNA promoter elements in the plasmid constructs is species specific; i.e., human rDNA promoter elements drive expression in human cells and not in mouse cells, and mouse rDNA promoter elements drive expression in mouse cells and not in human. Thus, the results favor the notion that the expression is Pol-I-specific.

To further test the specificity of species-specific expression in this system plasmid constructs were also prepared containing deletions that rendered the mouse rDNA promoter elements inoperative. As in the human system (Example 1, above), deletion of the Pol I-specific transcription initiation site (nucleotides −8 to +3) in the mouse rDNA promoter (pΔMENA) shows a large reduction in NPT expression supporting the premise that a majority of the NPT activity is derived from initiation of transcription by Pol I at authentic Pol I initiation sites in the constructs, rather than at cryptic Pol II sites.

EXAMPLE 3

Stable Expression of Pol-I-Specific Constructs

Previous reports have relied upon transient expression of a reporter gene in an rDNA promoter construct. It is well appreciated that transient expression does not always predict that a genetic construct will be capable of integrating into a cell genome in a manner that will permit stable expression. Therefore, the rDNA promoter plasmid constructs were also tested for their ability to provide stable expression of NPT once chromosomally integrated. When human cells were harvested for transient assays (Examples 1 and 2, above), a fraction of each transfected cell population ($5 \times 10^5$ cells) was replated in medium containing the neomycin analogue G418, i.e., to select for cells expressing neo. Stable expression of NPT protein was measured initially by scoring the number of G418 resistant colonies remaining after 7–10 days. (Other results recorded after 3 weeks are discussed below.) The results presented in FIG. 3 show the relative number of colonies obtained with each of the different plasmid constructs. (The numbers of colonies were also corrected for differences in the transfection efficiency of different cultures of cells.) A comparison was made of the number of colonies obtained with a strong Pol II-specific promoter plasmid construct, i.e., pLNX vector. For example, pLNX transfections commonly produced $5 \times 10^4$ G418 resistant colonies per transfected cell culture. The rDNA promoter elements in plasmid construct vectors generated stable colonies at a rate about 50% to 130% of the rate obtained with the Pol II-specific promoter (pLNX), i.e., pMENA= 127+/−60% and PHENA=51 +/−21% of the levels obtained with pLNX. Specificity of the rDNA promoter integrants was established in two ways: namely, 1) by testing species specificity; and, 2) by preparing promoter deletion mutants (as above). The results obtained are in agreement with the results obtained in the transient assays (Example 2, above): namely, long-term survival of neomycin resistant colonies mediated by the rDNA promoter plasmid constructs showed strong preference for expression in cells of the appropriate human or mouse species. In addition, deletion of the −8 to +3 transcription initiation site for Pol I reduced the number of surviving colonies to near background levels.

Stability of expression in the G418 resistant transformants:

NPT activity was also measured 7–10 days after selection (above) and then again after three weeks of growth in the absence of selection. rDNA-mediated NPT production was the same in both studies when compared by standardizing the values obtained to the levels of NPT produced by the pLNX vector.

In summary, the results show species-specificity for the expression of NPT from the rDNA promoter plasmids, and also that expression was dependent upon the sequence between −8 and +3 (i.e., a minimal eleven nucleotide initiation sequence) that is required for Pol I to initiate transcription in either a human or a murine cell. The results show that the constructs containing an rDNA promoter, an IRES element, and a PolyA signal are able to efficiently direct expression of NPT in these assays, and the expression is Pol I-specific, i.e., resulting from authentic Pol I transcription initiation sites and not cryptic Pol II initiation sites in the construct. The results are in contrast to previous reports in which rDNA promoters were shown to provide little, if any, production of translated message. In the results presented here, the inclusion of the IRES element unexpectedly appears to solve many of the problems encountered by others; i.e., by compensating for the lack of the normal cap site for ribosome binding and assembly the expression levels in co-transfection assays were brought up to the level achieved by a strong Pol II-promoter (i.e., pLNX), and in long-term assays stable expression was about 50% to about 300% of the level obtained with the strong Pol II promoter (Tables 3 and 4, below). The results also show that the insertion of a polyA downstream of the neo coding region also improved expression by 15-fold to about 50-fold, relative to the levels of expression obtained without polyA.

TABLE 3

Stable Expression of NPT Activity in G418 Selected Cells
NPT Activity*

| Construct | Human Cells | | Rat Cells | |
| --- | --- | --- | --- | --- |
| | Mean | Range | Mean | Range |
| pHENA | 37700 | 19600–60100 | nd | nd |
| pMENA | nd | nd | 8800 | 5950–16800 |
| pLNX | 53100 | 21200–67000 | 5900 | 2400–7200 |

*NPT activity in CPM/HR/μg protein

TABLE 4

Stable Expression in Selected Cells
Percentage of pLNX Activity

| Construct | Mean | Range |
| --- | --- | --- |
| pHENA | 71 | 30–130 |
| pMENA | 149 | 50–300 |

EXAMPLE 4

Nucleotide Sequences Stabilizing Transcript RNA

In these studies a surprising observation was made that genomic sites may exist for stabilizing transcript RNAs. Specifically, it was observed that the pHEN construct plasmids (i.e., lacking in the polyA element) yielded colonies at a level higher than background, but only in human cells. Since transient expression of NPT is low from the pHEN construct (FIG. 2a), it is considered possible that the colonies produced by this vector may result from integration of pHEN into the genome at relatively frequent integration sites that reside near genomic sites that are capable of providing a "signal" that substitutes for the SV40 polyA signal. In the latter case the "signal" would appear to be a nucleotide sequence transcribed at the 3' end of a transcript RNA that is capable of stabilizing the transcript, e.g., during transport from the nucleus to the cytoplasm.

Materials and Methods

Cells and Culture Conditions:

LNSV cells (human SV40 transformed, HPRT⁻ fibroblasts, Miller et al., 1983) and rat 208F fibroblasts (Quade, 1979) were cultured in a 10% $CO_2$/95% air environment, 100% humidity, in Dulbecco's Modification of Eagles Medium (DMEM) containing 4.5 g glucose/liter and supplemented with 10% fetal bovine serum and penicillin/streptomycin.

DNA Transfection:

Cells were plated at a density of $10^6$ cells per 10 cm tissue culture dish one day prior to transfection, and the medium was replaced with fresh medium immediately prior to transfection. Calcium phosphate/DNA precipitates (prepared as previously described by Corsaro and Pearson, 1981; and, Miller & Rosman, 1989) were added to each dish and the cells incubated for 24 hours. The medium containing the precipitate was then replaced with fresh medium and after an additional 24 hours the cells were either harvested for enzyme assays or passaged into medium containing G418 (0.5 mg/ml active concentration) to select for expression of the neomycin phosphotransferase (neo) gene.

Plasmids:

The following abbreviations are used herein to refer to plasmid elements: namely, E, for the IRES element; N, for neo element; M, for the mouse rDNA promoter and H, for the human rDNA promoter element; L, for the retroviral 5' LTR; S and A, for the SV40 polyA; and, Δ for deletion of nucleotides from a sequence.

Plasmids pEN and pENA:

An EcoRI to BamHI fragment that contains the entire coding region of the gene that confers resistance to neomycin (i.e., neomycin phosphotransfersse, neo) was subcloned from the plasmid pLNSX (Miller and Rosman, 1989) into the EcoRI to BamHI sites of the vector Bluescript SK+™ (Stratagene, S.D., Calif.). The sequences at the translation start site of neo was mutated to an NcoI restriction site by oligonucleotide-directed mutagenesis (Kunkel, 1985) using the oligonucleotide 5 '-AGGATCGTTTCCCAT GGTTGAACAAGAT-3'SEQ. I.D. NO. 1. Following mutagenesis, sequences upstream of the neo coding region, i.e., between the EcoRI site and the novel NcoI site, were removed and replaced with a 596 bp nucleotide sequence obtained from the EcoRI to NcoI restriction site of pCITE-1™ (Novagen). This fragment contains the internal ribosome entry site (IRES) nucleotide sequence from encephalomyocarditis virus (ECMV). The resulting plasmid was termed pEN, where E represents the IRES and N represents neo. Next, a 237 bp nucleotide BamHI to BclI fragment was prepared from pLNSX (above) that contains the polyadenylation (PolyA) signals from SV40 virus. This fragment was subcloned into the BamHI site, i.e., downstream from the neo coding region in the plasmid pEN, in an orientation that maintains an intact BamHI site between neo and the polyA signal. This plasmid was termed pENA, where A represents the SV40 polyA signal. (The neo element in this construct serves as a test nucleotide sequence inserted into the coding region of the plasmid construct.)

The plasmid pLNX was constructed by removing the BstBI to ClaI fragment from the retroviral construct pLNSX (Miller and Rosman, 1989). This plasmid vector utilizes a Moloney murine sarcoma virus promoter/enhancer to drive Pol II transcription of the neo coding sequences.

Plasmids pHENA and pΔHENA:

The plasmid prHu3 contains a human rDNA promoter fragment that extends from an EcoRI site at −500 to a BamHI site at +1500, i.e., positions relative to the transcription initiation site (+1) of rDNA, and as described by Learned and Tijan, 1982. The prHu3 plasmid was cut at a unique BstEII site (i.e., at +80), filled in using the Klenow fragment of DNA polymerase I, and then EcoRI linkers (CGGAATTCCG) SEQ. I.D. NO. 2 were added. Next, for cloning the rDNA promoter, an EcoRI promoter fragment (i.e., from −500 to the modified +80 site) was excised from the modified prHu3 vector and the fragment was inserted into pBluescript SK+™ (i.e., in an orientation such that the −500 EcoRI site is adjacent to the T7 promoter of the Bluescript vector); the vector was termed the pH vector. Next, nucleotides−8 to +3 in the human rDNA promoter were deleted by oligonucleotide-directed mutagenesis using a synthetic olginonucleotide with the following sequence: namely, 5'-GCATTTGGGCCGCCGACACGCTG TCCTCT-3' SEQ. I.D. NO. 3, the resultant plasmid was termed pΔH.

EcoRI fragments containing the human rDNA promoter in pH and pΔH were subcloned into pENA (above) in an orientation such that Pol I transcription of these rDNA promoters is directed towards the IRES and neo elements of the construct. The resulting plasmids were termed pHENA and pΔHENA.

pMENA and pΔMENA

Plasmid p5'-2150 that contains a mouse rDNA promoter element (i.e., from −2150 to +292) was a gift from Barbara Sollner-Webb, (see Kuehn and Arnheim, 1983 for sequence). The plasmid contains a unique StuI restriction site at (i.e., at −640) and an SmaI site (i.e., at +155). A restriction fragment was prepared from p5'-2150 by digestion with StuI and SmaI; EcoRI linkers (CGGAATTCCG) were added; and, an EcoRI fragment (i.e., from −640 to +155) was cloned into pBluescriptSK+™ (i.e., in an orientation such that the −640 EcoRI site was adjacent to the T7 promoter in the Bluescript vector); this plasmid was termed pM. Nucleotides −8 to +3 of the mouse rDNA promoter element were deleted by oligonucleotide-directed mutagenesis using an oligonucleotide with the following sequence: namely, 5'-CCTATTGGACCTGGGACACGCGGT CCTTTC-3' SEQ. I.D. NO. 4; the resultant plasmid was termed pΔM.

The EcoRI fragments contained within the mouse rDNA promoter element in pM and pΔM were subcloned into pENA (i.e., in an orientation such that Pol I directed transcription from the rDNA promoter element toward the IRES and neo elements. The resulting plasmids are termed pMENA and pΔMENA .

pΔENA and pHΔENA:

The pENA plasmid was cut at a unique PFlMI restriction site in the EMCV IRES element. After preparing blunt ends and ligating EcoRI linkers (CGGAATTCCG) the plasmid was digested with EcoRI and recircularized, i.e., resulting in deletion of 461 nucleotides from the 5' side of the EMCV IRES element. This plasmid was termed pΔENA. pHΔENA was constructed by inserting the respective human (H) rDNA promoter element into the EcoRI site in pΔENA (above).

pHEN and pMEN:

The SV40 polyA element present in pHENA and pMENA was removed by cutting these plasmids at a unique BstBI restriction site (i.e., located 18 nucleotides downstream from the translation stop codon of the neo element). Following blunt-ending and addition of XbaI linkers (CTCTAGAG) SEQ. I.D. NO. 5 the deletion plasmids were digested with XbaI and then recircularized. The procedure resulted in the deletion of sequences immediately downstream from the neo element and extending to the XbaI site in the polylinker region of the pBluescriptSK+™ plasmid. The plasmids prepared in this manner, and lacking the polyA element, were termed pHEN and pMEN, respectively, for the plasmids containing either the human or the mouse rDNA promoter.

pRSV-βgal pRSV-,βgal was kindly provided as a gift from Yuan Zhuang (FHCRC, Seattle, Wash.) and consists of a Rauscher sarcoma virus (RSV) prmoter (376 bp MluI-HindIII fragment from RSV-neo) linked to the entire E. coli β-galactosidase coding sequence (β-gal, 3040 bp BglII fragment from pJ3β-gal) followed by an SV40 poly adenylation signal (237 bp BclI-BamHl fragment from SV40). The combined expression elements were cloned between the SacI and XhoI sites in Bluescript II-SK+(Stratagene, La Jolla, Calif.)

Neomycin Phosphotransferase Assay

Cells growing at log phase were treated with trypsin and washed once with medium containing fetal bovine serum and twice with phosphate buffered saline. About $10^6$ cells were resuspended in 100µl of a lysis buffer containing 50 mM phosphate pH 8.0, 10 mM KCl, 1 mM $MgCl_2$, 50 mM β-mercaptoethanol, and then freeze/thawed three times (−70° C.). The cell lysates were then clarified by centrifugation for 15 minutes at maximum speed in a eppendorf microcentrifuge and aliquots of clarified supernatant assayed for neomycin phosphotransferase (NPT) activity. This was done by mixing 1–10 µl cell extract with 50 µl NPT reaction mix (67mM TRIS pH 7.1, 42 mM $MgCl_2$, 400 mM $NH_4Cl$, 1.2 µM ATP, 90 µg/ml neomycin sulfate, 20 µCi $\gamma^{32}$-P-ATP/ml). The reaction was then incubated for 1 hr at 37° C., then extracted with an equal volume of phenol/chloroform/2% isoamyl alcohol. Aliquots of the aqueous phase were spotted onto P81 ion-exchange paper and the paper washed extensively in 50 mM phosphate pH 7.5. NPT-mediated incorporation of $^{32}P$ into neomycin sulfate was determined by scintillation counting. NPT activity was expressed as CPM incorporated per µg cell protein per hour.

β-galactosidase Assay.

β-galactosidase activity was measured in clarified cell extracts (as prepared for NPT assays) by incubating aliquots of cell extract in ONPG reaction mix (50 mM phosphate pH 8.0, 10 mM KCl, 1 mM $MgCl_2$, 0.4 mg/ml o-nitrophenyl-β-D-galactopyranoside). The reaction was carried out at room temperature and the change in optical density at 410 nm measured over a period of 0.5 to 2.0 hours. β-galactosidase activity was expressed as the change in optical density per µg cell protein per hour.

Citations

1. Fleisher, S. and I. Grummt. 1983. Expression of an mRNA coding gene under the control of an RNA polymerase I promoter. EMBO J. 2: 2319–2322.
2. Grummt, I. and J. A. Skinner. 1985. Efficient transcription of a protein-coding gene from the RNA polymerase I promoter in transfected cells. Proc. Nat. Acad. Sci. USA 82: 722–726.
3. Smale, S. T. and R. Tijan. 1985. Transcription of Herpes Simplex virus tk sequences under the control of wild-type and mutant RNA polymerase I promoters. Mol. Cell. Biol. 5: 352–362.
4. Surmacz, E., 0. Ronning, L. Kaczmarek and R. Baserga. 1986. Regulation of the expression of the SV40 T-antigen coding gene under the control of an rDNA promoter. J. Cell. Phys. 127: 357–365.
5. Surmacz, E., L. Kaczmarek, 0. Ronning and R. Baserga. 1987. Activation of the ribosomal DNA promoter in cells exposed to insulinlike growth factor I. Mol. Cell. Biol. 7: 657–663.
6. Lopata, M. A., D. W. Cleveland and B. Sollner-Webb. 1986. RNA polymerase specificity of mRNA production and enhancer action. Proc. Nat. Acad. Sci. USA 83: 6677–6681.
7. Grummt, I. and J. A. Skinner. 1985. Efficient transcription of a protein-coding gene for the RNA polymerase I promoter in transfected cells. Proc. Nat. Acad. Sci. USA 82: 722–726.
8. Rudenko, G., H. -M. M. Chung, V. P. Pham and L. H. T. Van der Ploeg. 1991. RNA polymerase I can mediate expression of CAT and neo protein-coding genes in Trypanasoma brucei. EMBO J. 10: 3387–3397.
9. Zomerdijk, J. C. B. M., R. Kieft and P. Borst. 1991a. Efficient production of functional mRNA mediated by RNA polymerase I in Trypanosoma brucei. Nature 353: 772–775.
10. Zomerdijk, J. C. B. M., R. Kieft, P. G. Shiels and P. Borst. 1991b. Alpha-amanitin-resistant transcription units in trypanosomes: a comparison of promoter sequences for a VSG gene expression site and for ribosomal RNA genes. Nucl. Acids. Res. 19: 5153–5158.
11. Miller, A. D., Jolly, D. J., Friedmann, T., and Verma, I. M., 1983, A transmissible retrovirus expressing human hypoxanthine phosphoribosyl-transferase (HPRT): Gene transfer into cells obtained from humans deficient in HPRT. Proc. Natl. Acad. Sci. USA, 80:4709–4713
12. Miller, A. D. and Rosman, G. J., 1989, Improved retroviral vectors for gene transfer and expression. Bio Techniques 7:980–990.
13. Quade, K., 1979, Transformation of mammalian cells by avian myelocytomastosis virus and avian erythroblastosis virus. Virology 98:461–465
14. Corsaro, C. M. and Pearson, M. L., 1981, Enhancing the efficiency of DNA-mediated gene transfer in mammalian cells. Somatic Cell Genetic. 7:603–616
15. Kuehn, M. and N. Arnheim, 1983, Nucleic Acids Res. 11: 211–224.
16. Kunkel, T. A., 1985, Proc. Natl. Acad. Sci. USA. 82: 488–492.
17. Learned R. M., and R. T. Tjian, 1982, J. Mol. Appl. Gen. 1: 575–584.
18. Miller, A. D. and Rosman, G. J., 1989, Bio Techniques 7: 980–990.
19. Norton, P. A., and J. M. Coffin, 1985, Bacterial β-galactosidase as a marker of Rous sarcoma virus gene expression and replication. Mol. Cell Biol. 5:281–290.
20. Pikaard, et al., 1990, Enhancers for RNA polymerase I in mouse ribosomal RNA. Mol. Cell. Biol. 10: 4816–4825.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid comprising first, second, third, and fourth nucleotide sequences in serial array, wherein: the first nucleotide sequence is capable of hybridizing under stringent conditions to an RNA polymerase I-specific promoter from a eukaryotic ribosomal RNA gene and is capable of initiating RNA polymerase I-specific transcription of the second, third, and fourth nucleotide sequences, the second nucleotide sequence is capable of hybridizing under stringent conditions to an internal ribosome entry signal and encodes RNA capable of binding with the translation initiation complex in a mammalian cell such that the third nucleotide sequence is translated; the third nucleotide sequence comprises a coding region; and the fourth nucleotide sequence comprises a polyA signal.

2. A process for obtaining Pol I-specific expression of the coding region of claim 1 in a permissive cell, comprising introducing the nucleic acid of claim 1 into the permissive cell.

3. The process of claim 2, wherein the Pol I-specific expression level of the coding region in the permissive cell is equal to or higher than the Pol II-specific expression level achievable by introducing into a test cell, of the same type as said permissive cell, a nucleic acid consisting essentially of a Pol II promoter and the second, third, and fourth nucleotide sequences in serial array.

4. A cell obtained by the process of claim 2.

5. An isolated nucleic acid comprising first, second, third, and fourth nucleotide sequences in serial array, wherein: the first nucleotide sequence is capable of hybridizing under stringent conditions to an RNA polymerase I-specific promoter from a eukaryotic ribosomal RNA gene and is capable of initiating RNA polymerase I-specific transcription of the second, third, and fourth nucleotide sequences; the second nucleotide sequence is capable of hybridizing under stringent conditions to an internal ribosome entry signal and encodes RNA capable of binding with the translation initiation complex in a mammalian cell such that the third nucleotide sequence is translated; the third nucleotide sequence comprises a linker region capable of accepting a gene of interest; and the fourth nucleotide sequence comprises a polyA signal.

\* \* \* \* \*

UNITED STATES PATENT AND TRADEMARK OFFICE
CERTIFICATE OF CORRECTION

PATENT NO.     : 6,368,862 B1
DATED          : April 9, 2002
INVENTOR(S)    : T.D. Palmer et al.

It is certified that error appears in the above-identified patent and that said Letters Patent is hereby corrected as shown below:

<u>Title page,</u>
Item [75], Inventors, "Kirland," should read -- Kirkland --
Item [74], *Attorney, Agent or Firm* "Christensen, O'Connor, Johnson Kindness PLLC" should read -- Christensen O'Connor Johnson Kindness PLLC --

<u>Column 2,</u>
Line 2, "Poll" should read -- Pol I --
Line 21, "5-to" should read -- 5- to --

<u>Column 3,</u>
Line 15, "β-amanitin" should read -- α-amanitin --
Line 33, "sequenc." should read -- sequence --
Line 45, "FEb." should read -- Feb. --

<u>Column 7,</u>
Line 5, "78" should read -- +78 --
Lines 51-52, "a amanitin" should read -- α-amanitin --

<u>Column 9,</u>
Line 43, "3'-G-5' ppp5-Terminal" should read -- 3'-G-5'ppp5-Terminal --

<u>Column 14,</u>
Line 38, "specificity." The" should read -- specificity." The --

<u>Column 19,</u>
Line 34, "3'of" should read -- 3' of --
Line 52, "(MOMSV)" should read -- (MoMSV) --
Line 54, "co-transfecting  µg" should read -- co-transfecting 10 µg --

<u>Column 20,</u>
Table 1, following line 4, following the line which begins "pHEN" insert a line which crosses the width of the table.
Table 1, following line 10, following the line which begins "pEN" insert a line which crosses the width of the table.
Table 1, following line 11, following the line which begins "pLNX" insert a line which crosses the width of the table.

<u>Column 22,</u>
Table 3, following line 2, following the line which begins "pMENA" insert a line which crosses the width of the table.

UNITED STATES PATENT AND TRADEMARK OFFICE
CERTIFICATE OF CORRECTION

PATENT NO. : 6,368,862 B1
DATED : April 9, 2002
INVENTOR(S) : T.D. Palmer et al.

It is certified that error appears in the above-identified patent and that said Letters Patent is hereby corrected as shown below:

Column 23,
Line 40, "phosphotransfersse," should read -- phosphotransferase, --
Line 42, "SK+$^{TM}$" should read -- SK$^{+TM}$ --
Line 46, "5'-AGGATTCCCAT" should read -- 5'-AGGATTCCCAT --
Line 47, "-3'SEQ." should read -- -3' SEQ. --

Column 24,
Line 13, after "No. 2" insert -- , --
Line 17, "SK+$^{TM}$" should read -- SK$^{+TM}$ --
Line 20, "nucleotides-8" should read -- nucleotides -8 --
Line 23, "5'-GCATTTGGGCCGCCGACACGCTGTCCTCT-3'" should read
-- 5'-GCATTTTGGGCCGCCGACACGCTGTCCTCT-3' --
Line 42, "SK+$^{TM}$" should read -- SK$^{+TM}$ --

Column 25,
Line 11, "SK+$^{TM}$" should read -- SK$^{+TM}$ --
Line 17, "pRSV-,βgal" should read -- pRSV-βgal --
Line 21, "BgIII" should read -- BglII --
Line 22, "pJ3β-gal)" should read -- pJ3-β-gal) --
Line 23, "BcII-BamHl" should read -- BclI-BamHI --
Line 25, "SK+$^{TM}$" should read -- SK$^{+TM}$ --

UNITED STATES PATENT AND TRADEMARK OFFICE
CERTIFICATE OF CORRECTION

PATENT NO.    : 6,368,862 B1
DATED         : April 9, 2002
INVENTOR(S)   : T.D. Palmer et al.

It is certified that error appears in the above-identified patent and that said Letters Patent is hereby corrected as shown below:

Column 26,
Lines 5 and 9, "0. Ronning" should read -- O. Ronning --
Line 22, "H. -M." should read -- H.-M. --

Column 29,
Line 40, "sequences," should read -- sequences; --

Signed and Sealed this

Fifteenth Day of April, 2003

JAMES E. ROGAN
*Director of the United States Patent and Trademark Office*